US007368248B2

(12) United States Patent
Echeverri et al.

(10) Patent No.: US 7,368,248 B2
(45) Date of Patent: May 6, 2008

(54) EUKARYOTIC CELL DIVISION GENES AND THEIR USE IN DIAGNOSIS AND TREATMENT OF PROLIFERATIVE DISEASES

(75) Inventors: Christophe Echeverri, Dresden (DE); Pierre Goenczy, Lausanne (CH); Anthony Hyman, Dresden (DE); Steven Jones, Vancouver (CA); Karen Oegema, La Jolla, CA (US); Matthew Kirkham, Brisbane (AU)

(73) Assignee: Cenix Bioscience GmbH, Dresden (DE)

( * ) Notice: Subject to any disclaimer, the term of this patent is extended or adjusted under 35 U.S.C. 154(b) by 498 days.

(21) Appl. No.: 10/415,657

(22) PCT Filed: Nov. 9, 2001

(86) PCT No.: PCT/EP01/13034

§ 371 (c)(1),
(2), (4) Date: Sep. 8, 2003

(87) PCT Pub. No.: WO02/38805

PCT Pub. Date: May 16, 2002

(65) Prior Publication Data

US 2004/0048277 A1   Mar. 11, 2004

Related U.S. Application Data

(60) Provisional application No. 60/246,750, filed on Nov. 9, 2000.

(51) Int. Cl.
*G01N 33/53* (2006.01)
(52) U.S. Cl. ........................................................ 435/7.1
(58) Field of Classification Search .................... None
See application file for complete search history.

(56) References Cited

U.S. PATENT DOCUMENTS

| 5,155,037 A | 10/1992 | Summers |
| 5,162,222 A | 11/1992 | Guarino et al. |
| 6,639,063 B1 * | 10/2003 | Edwards et al. ............ 536/23.5 |

FOREIGN PATENT DOCUMENTS

EP   0 397 485 A1   11/1990

OTHER PUBLICATIONS

Scott et al, Nature Genetics, 1999, 21:440-443).*
Skolnick et al, 2000, Trends in Biotech. 18:34-39.*
Bork, 2000, Genome Research 10:398-400.*
Doerks et al, 1998, Trends in Genetics 14:248-250.*
Smith et al, 1997, Nature Biotechnology 15:1222-1223.*
Brenner, 1999, Trends in Genetics 15:132-133.*
Bork et al, 1996, Trends in Genetics 12:425-427.*
Bowie et al, 1990, Science 247:1306-1310.*

Hitzeman et al., "Isolation and Characterization of the Yeast 3-Phosphoglycerokinase Gene (PKG) by an Immunological Screening Technique", *The Journal of Biological Chemistry* (Dec. 25, 1980), vol. 255, No. 24, pp. 12073-12080.
Vasudevan et al., "Muscarinic acetylcholine receptor produced in recombinant baculovirus infected sf9 insect cells couples with endogenous G-proteins to activate ion channels", *FEBS* (Oct. 1992), vol. 311, No. 1, pp. 7-11.
Palmiter et al., "Metallothionein-Human GH Fusion Genes Stimulate Growthh of Mice," *Science* (1983), vol. 222, pp. 809-814.
Subramani et al., "Expression of the Mouse Dihydrofolate Reductase Complementary Deoxyribonucleic Acid in Simian Virus 40 Vectors", *Molecular and Cellular Biology* (Sep. 1981), vol. 1, No. 9, pp. 854-864.
Russell et al., "DNA sequence of two yeast promoter-up mutants", *Nature* (1983), vol. 304, pp. 652-654.
Sulston et al., "The Embryonic Cell Lineage of the Nematode *Caenorhabditis elegans*", *Developmental Biology* (1983), vol. 100, pp. 64-119.
Sluder et al., "Control of centrosome reproduction: The right number at the right time", *Biology of the Cell* (1999), vol. 91, pp. 413-427.
Database EMBL 'Online! EMBL-EBI; Jun. 23, 1998, The *C. Elegans* Sequencing Consortium: "Genome sequence of the nematode *C. elegans*: a platform for investigating biology", Database accession No. AL 024499, XP002199986.
Database Genbank 'Online! NCBI; Oct. 25, 2000, The *C. Elegans* Sequencing Consortium: "Genome sequence of the nematode *c. elegans*: a platform for investigating biology", Database accession No. AL024499, XP002199987.
The *C. Elegans* Sequencing Consortium: Genome sequence of the nematode *C. elegans*: A platform for investigating biology, Science (Washington DC), vol. 282, No. 5396, Dec. 11, 1998, pp. 2012-2018, XP002199976, ISSN: 0036-8075.
Kaitna, Susanne et al., "Incenp and an Aurora-like kinase form a complex essential for chromosome segregation and efficient completion of cytokinesis." Current Biology, vol. 10, No. 19, Sep. 15, 2000, pp. 1172-1181, XP002199977, ISSN: 0960-9822.
Boxem Mike et al., "The *Caenorhabditis elegans* gene ncc-1 encodes a cdc2-related kinase required for M phase in meiotic and mitotic cell divisions, but not for S phase." Development (Cambridge), vol. 126, No. 10, May 1999, pp. 2227-2239, XP002199978, ISSN: 0950-1991.
Hong Yang et al., "Developmental regulation of a cyclin-dependent kinase inhibitor controls postembryonic cell cycle progression in *Caenorhabditis elegans*." Development (Cambridge), vol. 125, No. 18, 1998, pp. 3585-3597, XP002199979, ISSN: 0950-1991.

(Continued)

*Primary Examiner*—Misook Yu
*Assistant Examiner*—Mark Halvorson
(74) *Attorney, Agent, or Firm*—Foley & Lardner LLP

(57) ABSTRACT

The present invention relates to the significant functional role of several *C. elegans* genes and of their corresponding gene products in cell division and proliferation processes that could be identified by means of RNA-medicated interference (RNAi) and to the identification and isolation of functional orthologues of said genes including all biologically-active derivatives thereof. The invention further relates to the use of said gene products (including said orthologues) in the development or isolation of anti-proliferative agents, particularly their use in appropriate screening assays, and their use for diagnosis and treatment of proliferative diseases.

2 Claims, 5 Drawing Sheets

OTHER PUBLICATIONS

Goenczy et al., "Large-scale Screening for Genes Required for Cell Division in *C. elegans*." Press Book 39. ASCB Annual Meeting Slected Biomedical Abstracts, Dec. 11-15, 1999, Washington, D.C., 'Online!, XP002199980, Retrieved from the Internet: <URL:http://www.ascb.org/meetings/am99/pressbk99.pdf>, retrieved on May 23, 2002.

Goenczy Pierre et al., "Dissection of cell divisions processed in the one cell stage *Caenorhabditis elegans* embryo by mutational analysis." Journal of Cell Biology, vol. 144, No. 5, Mar. 8, 1999, pp. 927-946, XP002199981, ISSN: 0021-9525.

Fire Andrew et al., "Potent and specific genetic interference by double-stranded RNA in *Caenorhabditis elegans*." Nature (London), vol. 391, No. 6669, Feb. 19, 1998, pp. 806-811, XP002199982, ISSN: 0028-0836.

Fraser Andrew et al., "Functional genomic analysis of *C. elegans* chromosome I by systematic RNA interference." Nature (London), vol. 408, No. 6810, Nov. 16, 2000, pp. 325-330, XP002199983, ISSN: 0028-0836.

Goenczy Pierre et al., "Functional genomic analysis of cell division in *C. elegans* using RNAi of genes on chromosome III." Nature (London), vol. 408, No. 6810, Nov. 16, 2000, pp. 331-336, XP002199984, ISSN: 0028-0836.

Waterson, R. "*Caenorhabditis elegans* cosmid C02F5, complete sequence", Database EMBL 'Online! EBI; May 9, 1993, Database accession No. L14745, XP002212273.

Wilson et al., "2.2 Mb of contiguous nucleotide sequence from chromosome III of *C. elegans*", Nature, vol. 368, Mar. 3, 1994, pp. 32-38, XP002014926.

Waterson R., "*Caenorhabditis elegans* cosmid F10E9, complete sequence", Database EMBL 'Online! EBI; Feb. 16, 1993, Database accession No. L10986, XP002212274.

Kohara Y., "*C. elegans* cDNA clone yk352b6: 5' end, single read." Database EMBL 'Online!, Database accession No. C64048, XP002212275.

McCombie et al., "West00235 Mixed Stage, Stratagene (cat #937006) *Caenorhabditis elegans* cDNA clone CEMS47, mRNA sequence." Database EMBL 'Online! EBI; Aug. 16, 1997, Database accession No. M79698, XP002212276.

Mas et al., "Cloning and expression analysis of a novel gene, RP42, mapping to an autisn susceptibility locus on 6g16", Database EMBL 'Online! EMBL-EBI; Aug. 17, 2000, Database accession No. AF292100, XP002199988, & Genomics, vol. 65, Apr. 1, 2000, pp. 70-74, XP002199985..

Khelfaoui Malik et al., "Early neuronal and glial determination from mouse E10.5 telencephalaon embryonic stem cells: An in vitro study." NEUROREPORT, vol. 13, No. 9, 2002, pp. 1209-1214, XP001095765, Jul. 2, 2002, ISSN: 0959-4965.

* cited by examiner

Multiple Sequence Alignment of the H38K22.2a family

```
CeH38K22.2a    ---MNRLKS-DQKTKLRQFVQWICVTEAVSLNFLAKANWNIEYAMTLYFDNPNLFAGSTP
CeH38K22.2b    ---MNRLKS-DQ------------------------------------------------
DmCG7427       MILQNKLKSSTHRDKVKKFISLEHTGEQTALFCLQQNDWKFELASDNYFQNBEYYYRE--
MmAAF04863     ---MNKLKS-SQKDKVRQFMIFTQSSEKTAVSCLSQNDWKLDVATDNFFQNPELYIRESV
HsAAH09478     ---MNKLKS-SQKDKVRQFMIFTQSSEKTAVSCLSQNDWKLDVATDNFFQNPELYIRESV

CeH38K22.2a    QPSVDRSNIERLFNQYVDPKDKVGEKRMGPHGINRLLTDLGYEATDRRVLVLAWKFTAQT
CeH38K22.2b    -----KTKIERLFNQYVDPKDKVGEKRMGPHGINRLLTDLGYEATDRRVLVLAWKFTAQT
DmCG7427       ---LDRKRIEQLFMRYRDPSD---PLKIGSQGVIHFLEDLDLKPDSKLVLIIAWKFHAEV
MmAAF04863     KGSLDRKKLEQLYTRYKDPQD---ENKIGIDGIQQFCDDLALDPASISVLIIAWKFRAAT
HsAAH09478     KGSLDRKKLEQLYNRYKDPQD---ENKIGIDGIQQFCDDLALDPASISVLIIAWKFRAAT

CeH38K22.2a    QCEFSLDEWVKGMTALQADTVQNLRQRIDSINSGLESDKAKFHELYLFAFNYAKSAACRN
CeH38K22.2b    QCEFSLDEWVKGMTALQADTVQNLRQRIDSINSGLESDKAKFHELYLFAFNYAKSAACRN
DmCG7427       QCEFSRDEFINGMCDLGIDSIDKLKTKLPILEQELN-DAGKEKDFYHFTENYAKDPGQKG
MmAAF04863     QCEFSKQEFMDGMTELGCDSIEKLKAQLPKMEQELK-EPGRFKDFYQFTFNFAKNPGQKG
HsAAH09478     QCEFSKQEFMDGMTELGCDSIEKLKAQLPKMEQELK-EPGRFKDFYQFTFNFAKNPGQKG

CeH38K22.2a    LDLETAICCWDVLFGQRSTIMTQWIDFEWAQENAAASRLAQNVGASNAKQFKSVWISRDT
CeH38K22.2b    LDLETAICCWDVLFGQRSTIMTQWIDFEWAQENAAASRLAQNVGASNAKQFKSVWISRDT
DmCG7427       IDLEMALAYWCIVLSGRFKFLDIWCQFEEEKHKRAIS--------------------RDT
MmAAF04863     LDLEMAIAYWNLVLNGRFKFLDLWNKFLLEHHKRSIP--------------------KDT
HsAAH09478     LDLEMAIAYWNLVLNGRFKFLDLWNKFLLEHHKRSIP--------------------KDT

CeH38K22.2a    WNLFWDFILLSKPDLSDYDDEGAWPVLIDQFVDYCRENLNYPKPGNASNDQQMETPKIAQ
CeH38K22.2b    WNLFWDFILLSKPDLSDYDDEGAWPVLIDQFVDYCRENLNYPKPGNASNDQQMETPKIAQ
DmCG7427       WNLLLDFATNIDDRMSNYDSEGAWPVLIDDFVEWCQENDHLKEDSSPASGYQQQSSASSS
MmAAF04863     WNLLLDFSSMIADDMSNYDEEGAWPVLIDDFVEFARPQIAGTKSTTV-------------
HsAAH09478     WNLLLDFSTMIADDMSNYDEEGAWPVLIDDFVEFARPQIAGTKSTTV-------------

CeH38K22.2a    KKPGIFYFNSNLQLIEFKLFQYPMLKTIFKITIHTAGTNR
CeH38K22.2b    KKPGIFYFNSNLQLIEFKLFQYPMLKTIFKITIHTAGTNR
DmCG7427       SQKNISSAYQTSHSTNYNYG--------------------
MmAAF04863     ----------------------------------------
HsAAH09478     ----------------------------------------
```

| Statistics | HsAAH09478 | MmAAF04863 | DmCG7427 |
|---|---|---|---|
| CeH38K22.2a | E-value: 1e-49<br>Identities: 101/275 (36%)<br>Positives: 158/275 (56%) | E-value: 7e-49<br>Identities: 100/275 (36%)<br>Positives: 157/275 (56%) | E-value: 6e-44<br>Identities: 104/299 (36%)<br>Positives: 154/299 (56%) |
| CeH38K22.2b | E-value: 1e-35<br>Identities: 78/214 (36%)<br>Positives: 118/214 (54%) | E-value: 7e-35<br>Identities: 77/214 (35%)<br>Positives: 117/214 (56%) | E-value: 2e-36<br>Identities: 86/238 (36%)<br>Positives: 126/238 (52%) |

FIG. 5

EUKARYOTIC CELL DIVISION GENES AND THEIR USE IN DIAGNOSIS AND TREATMENT OF PROLIFERATIVE DISEASES

In a first aspect, the present invention is related to the significant functional role of several *C. elegans* genes and of their corresponding gene products in cell division and proliferation processes that could be identified by means of RNA-mediated interference (RNAi).

In a second aspect, the invention relates to the identification and isolation of functional orthologues of said genes and their gene products found in other eukaryotic species, in particular man, including all biologically-active derivatives thereof.

In a third aspect, the present invention includes the use of said genes and gene products (including said orthologues) in the development or isolation of anti-proliferative agents for instance their use in appropriate screening assays and in methods for diagnosis and treatment of proliferative diseases.

In a forth aspect, the invention relates to antibodies to said gene products and their use in the development or isolation of anti-proliferative agents and in methods for diagnosis and treatment of proliferative diseases.

In a fifth aspect, the present invention is related to the use of these genes and gene products for developing structural models or other models for evaluating drug binding and efficacy as well as to any other uses which are derived from the new functions described here and which will become apparent from the disclosure of the present application for any person skilled in the art.

Metazoan cell division consists of an extremely complex, highly regulated set of cellular processes which must be tightly co-ordinated, perfectly timed, and closely monitored in order to ensure the correct delivery of cellular materials to daughter cells. Defects in these processes are known to cause a wide range of so-called proliferative diseases, including all forms of cancer. Since cell division represents one of the few, if not the only cellular process that is common to the aetiology of all forms of cancer, its specific inhibition has long been recognised as a preferred site of therapeutic intervention. Although mitotic inhibitor drugs are recognised as one of the most promising classes of chemotherapeutic agent, screening attempts to find new drug candidates in this class have been undermined by the strong inherent tendency of such screens to identify agents that target a single protein, tubulin. Tubulin polymerises to form microtubules, the primary cytoskeletal elements needed for mitotic spindle function and chromosome segregation. Microtubule functions, however, are ubiquitously needed in almost all cell types, whether dividing or not, a fact which therefore explains many of the unwanted side effects caused by antitubulin drugs.

Perhaps the best known example of a highly successful anti-neoplastic drug that targets tubulin is provided by paclitaxel, and its marketed derivative, Taxol, from Bristol Meyers Squibb. Its applicability has indeed been seriously limited by difficulties in determining an adequate dosing regimen due to a range of problematic side effects. Taxol treatment has resulted in anaphylaxis and severe hypersensitivity reactions characterised by dyspnea and hypotension requiring treatment, angioedema, and generalised urticaria in 2-4% of patients in clinical trials. All Taxol is administered after pretreatment with corticosteroids and despite pretreatment, fatal reactions have occurred. Severe conductance abnormalities resulting in life-threatening cardiac arrhythmia occur in less than 1 percent of patients and must be treated by insertion of a pacemaker. Taxol can cause fetal harm or fetal death in pregnant women. Furthermore, administration is commonly accompanied by tachycardia, hypotension, flushing, skin reactions and shortness-of-breath (mild dypsnea).

Despite these shortcomings, Taxol has been hailed by many as the most successful new anti-cancer therapeutic of the last three decades. Clearly, there is good justification for attempting to add to the list of mitotic inhibitors used to treat cancer. However, additional drugs that target tubulin or interfere with microtubule dynamics may be expected to have similar applicability and limitations as Taxol.

The task of the present invention therefore is to find new potential target proteins/genes for therapeutical drugs other than tubulin that are essential for completion of mitosis. These proteins/genes may provide novel targets to screen for new anti-neoplastic or cytotoxic anti-cancer agents.

Unfortunately, until now, the systematic identification of such target proteins/genes using genetic screening methods has been difficult in metazoans, and has relied heavily on the use of the unicellular yeast. Several major advances in the use of certain metazoan model organisms, particularly the nematode worm *Caenorhabditis elegans*, have now begun to offer new ways of bridging this gap.

The above-mentioned task of the invention to find new potential target proteins/genes for therapeutical drugs other than tubulin involved in mitosis processes is solved by a screening assay in *C. elegans* based on 'genomic RNA mediated interference (RNAi)' combined with a highly probative microscopic assay for documenting the first rounds of embryonic cell division (Sulston et al., The embryonic cell lineage of the nematode *Caenorhabditis elegans*. *Dev. Biol*. 100, 64-119 (1983); Gönczy et al., Dissection of cell division processes in the one cell stage *Caenorhabditis elegans* embryo by mutational analysis. *J Cell Biol* 144, 927-946 (1999)). With this combination of techniques a selected gene and also a variety of selected genes can be functionally characterized with unprecedented speed and efficiency.

The nematode *C. elegans* exhibits an almost entirely translucent body throughout its development, thereby offering unparalleled microscopic access for exquisitely detailed cytological documentation, even for the earliest steps of embryogenesis. This important feature, along with its short life cycle (3-5 days), its ease of cultivation, and its low maintenance costs, has helped make *C. elegans* arguably the best studied of all metazoans. Also, sequence data are now available for over 97% of the *C. elegans* genome (*C. elegans* Sequencing Consortium. Genome sequence of the nematode *C. elegans*: a platform for investigating biology. *Science* 282, 2012-2018 (1998)). Thus, *C. elegans* has proven to be an ideal organism for applying the new technique of RNA-mediated interference (RNAi). This technique consists in the targeted, sequence-specific inhibition of gene expression, as mediated by the introduction into an adult worm of double-stranded RNA (dsRNA) molecules corresponding to portions of the coding sequences of interest (Fire et al., Potent and specific genetic interference by double-stranded RNA in *Caenorhabditis elegans. Nature* 391, 806-811 (1998)). For the vast majority of *C. elegans* genes tested to date, this has been shown to yield a sequence-specific inhibition of the targeted gene's expression, accompanied by clearly detectable loss of function phenotypes in the treated worm's F1 progeny (and even in some cases, in the treated worm itself).

A large-scale RNAi technique-based screen was performed for 2,232 (that means 96%) of the predicted open reading frames on chromosome III of *C. elegans* which is described in detail in Gönczy et al., "Functional genomic analysis of cell division in *C. elegans* using RNAi of genes on chromosome III" Nature 408, 331-336 (2000). For the performance of this large-scale screen double-stranded RNA corresponding to the individual open reading frames was produced and micro-injected into adult *C. elegans* hermaphrodites, and the resulting embryos were analysed 24 hours later using time-lapse DIC microscopy.

Besides others, the *C. elegans* genes H38K22.2 (Genbank/EMBL ID: AL024499, provided in SEQ ID NO. 1-3), C02F5.1 (Genbank/EMBL ID: L14745; provided in SEQ ID NO. 4 and 5) and F10E9.8 (GenBank/EMBL ID: L10986; provided in SEQ ID NO. 6 and 7) gave rise to a phenotype detectable by the DIC-assay implying a functional role of these genes in metazoan cell division processes.

In at least one case (for H38K22.2) it had also been possible to identify a structurally and functionally homologous gene, a so-called orthologous gene, in another species, in particular *Homo sapiens*, namely the human orthologue RP42.

For the mouse orthologue of the RP42 gene it had merely been known that the gene shows a strongly developmentally regulated expression, particularly in proliferating neuroblasts from which neocortical neurons originate (Mas et al., "Cloning and expression of a novel gene, RP42, mapping to an autism susceptibility locus on 6Q16" Genomics 1; 65 (1), 70-74 (2000)). The functional role of RP42 in cell division and proliferation processes that makes it an excellent tool for the development or identification of drugs for diagnosis and/or therapy of proliferative diseases was not known so far.

With the essential function of said genes in cell division and proliferation known, these newly identified target genes and their corresponding gene products, any homologues, orthologues and derivatives thereof represent excellent tools for use in the development and isolation of a wide range of therapeutics including anti-proliferative agents and in the development of methods for diagnosis and treatment of proliferative diseases.

Therefore, in a first aspect, the present invention relates to isolated nucleic acid molecules encoding a polypeptide functionally involved in cell division and proliferation or a fragment thereof and comprising a nucleic acid sequence selected from the group consisting of:

(a) the nucleic acid sequences presented in SEQ ID NO. 1 to 3, SEQ ID NO. 4 to 5, SEQ ID NO. 6 to 7, SEQ ID NO. 12 and fragments thereof and their complementary strands, (b) nucleic acid sequences encoding polypeptides that exhibit a sequence identity with SEQ ID NO. 8, SEQ ID NO. 9, SEQ ID NO. 10, SEQ ID NO. 11 or SEQ ID NO. 13 of at least 25% over 100 residues and/or which are detectable in a computer aided search using the blast sequence analysis programs with an e-value of at most $10^{-3}$, (c) nucleic acid sequences which are capable of hybridizing with the nucleic acid sequences of (a) or (b) under conditions of medium stringency, (d) nucleic acid sequences which are degenerate as a result of the genetic code to any of the sequences defined in (a), (b) or (c).

The above mentioned fragments of the isolated nucleic acid molecules may comprise a at least 15 nucleotides and preferably at least 20 nucleotides.

Additionally the above mentioned isolated nucleic acid molecules may be single or double-stranded DNA-molecules as well as single- or double-stranded RNA-molecules.

a):

The nucleic acid sequences of those nucleic acid molecules encoding a polypeptide functionally involved in cell division and proliferation as mentioned in a) are provided in the sequence listing as SEQ ID NO. 1-3 (*C. elegans* genes H38K22.2 (Genbank/EMBL ID: AL024499)), as SEQ ID NO. 4 and 5 (*C. elegans* gene C02F5.1 (Genbank/EMBL ID: L14745)), as SEQ ID NO. 6 and 7 (*C. elegans* gene F10E9.8 (GenBank/EMBL ID: L10986)) and as SEQ ID NO. 12 (the human H38K22.2 orthologue, the RP42 protein (NCBI Accession No. AF292100).

The corresponding deduced amino acid sequences of these target genes are disclosed in SEQ ID NO. 8 (for H38K22.2a), in SEQ ID NO. 9 (for H38K22.2b), in SEQ ID NO. 10 (for C02F5.1), in SEQ ID NO. 11 (for F10E9.8) and in SEQ ID NO. 13 (for RP42).

b):

Additionally, the present invention also comprises isolated nucleic acid molecules that are structurally and functionally homologous counterparts (particularly orthologues) of at least one of said target genes as disclosed in SEQ ID NO 1 to 7 or 12.

Those homologous nucleic acid molecules may encode polypeptides that exhibit a sequence identity with SEQ ID NO. 8, SEQ ID NO. 9, SEQ ID NO. 10, SEQ ID NO. 11 or SEQ ID NO. 13 of at least 25% over 100 residues, preferably of at least 30% over 100 residues, more preferably of at least 35% over 100 residues and most preferably at least 40% over 100 residues.

FIG. 5 shows hat the aforementioned sequence identities are signifcant homologies that are appropriate to identify a polypeptide as an orthologue of the target proteins as depicted in SEQ ID NO. 8-11, and 13. FIG. 5 shows a multiple sequence alignment of the H38K22.2a family on protein level generated with a BLAST sequence analysis program. In this alignment the two *C. elegans* splice variants H38K22.2a and H38K22.b are compared to their corresponding orthologues in Drosophila (CG7427), in mouse (AAF04863) and in *Homo sapiens* (AAH09478). The statistics in FIG. 5 for the alignments show that the sequence identity on protein level between the *C. elegans* clone H38K22.2a and its human orthologue (AAH09478) is 36% over 299 residues. Similarly, the sequence identities between *C. elegans* clone H38K22.2b (the other splice variant) and its human orthologue is 36% over 238 residues. It is obvious to anyone skilled in the art that these sequence homologies are significant homologies and that therefore the human clone with the accession No. AAH09478 is unambiguously identified as the human orthologue of the *C. elegans* clones H38K22.2a and H38K22.b.

The invention also comprises isolated nucleic acid molecules that are detectable in a computer aided search using one of the BLAST sequence analysis programs with an e-value of at most $10^{-30}$, preferably with an e-value of at most most $10^{-35}$, more preferably with an e-value of at most most $10^{-40}$.

FIG. 5 shows that the aforementioned e-values characterize signifcant sequence homologies that are appropriate to identify a polypeptide as an orthologue of the target proteins as depicted in SEQ ID NO. 8-11, and 13.

The BLAST sequence analysis programs are programs used for sequence analysis that are publically available and known to anyone skilled in the art. When sequence alignments are done by a BLAST sequence analysis program, most of those programs calculate so called "e-values" to characterize the grade of homology between the compared sequences. Generally a small e-value characterizes a high sequence identity/homology, whereas larger e-values characterize lower sequence identities/homologies.

"Homology" means the degree of identity between two known sequences. As stated above, homologies, that means sequence identities, may suitably be determined by means of computer programs known in the art. The degree of homology required for the sequence variant will depend upon the intended use of the sequence. It is well within the capability of a person skilled in the art to effect mutational, insertional and deletional mutations which are designed to improve the function of the sequence or otherwise provide a methodological advantage.

c):

The present invention further relates to isolated nucleic acid sequences or fragments thereof which are capable of hybridizing with the nucleic acid sequences of (a) or (b) under conditions of medium/high stringency.

The grade of sequence identity between a first and a second nucleic acid molecule can also be characterized by the capability of the first nucleic acid molecule to hybridize under certain conditions to a second nucleic acid molecule.

Suitable experimental conditions for determining whether a given DNA or RNA sequence "hybridizes" to a specified polynucleotide or oligonucleotide probe involve presoaking of the filter containing the DNA or RNA to examine for hybridization in 5×SSC (sodium chloride/sodium citrate) buffer for 10 minutes, and prehybridization of the filter in a solution of 5×SSC, 5×Denhardt's solution, 0,5% SDS and 100 mg/ml of denaturated sonicated salmon sperm DNA (Maniatis et al., 1989), followed by hybridization in the same solution containing a concentration of 10 ng/ml of a random primed (Feinberg, A. P. and Vogelstein, B. (1983), *Anal. Biochem.* 132:6-13), $^{32}$P-dCTP-labeled (specific activity>1×10$^9$ cpm/µg) probe for 12 hours at approximately 45° C. The filter is then washed twice for 30 minutes in 2×SSC, 0,5% SDS at at least 55° C. (low stringency), at least 60° C. (medium stringency), preferably at least 65° C. (medium/high stringency), more preferably at least 70° C. (high stringency) or most preferably at least 75° C. (very high stringency). Molecules to which the probe hybridizes under the chosen conditions are detected using an x-ray film.

d):

The present invention further relates to isolated nucleic acid molecules or fragments thereof which are degenerate as a result of the genetic code to any of the sequences defined in (a), (b) or (c).

The application of automated gene synthesis provides an opportunity for generating sequence variants of the naturally occurring genes. It will be appreciated, for example, that polynucleotides coding for the same gene products can be generated by substituting synonymous codons for those represented in the naturally occurring polynucleotide sequences as identified herein. Such sequences will be referred to as "degenerate" to the naturally occurring sequences. In addition, polynucleotides coding for synthetic variants of the corresponding amino acid sequences can be generated which, for example, will result in one or more amino acids substitutions, deletions or additions. Also, nucleic acid molecules comprising one or more synthetic nucleotide derivatives (including morpholinos) which provide said nucleotide sequence with a desired feature, e.g. a reactive or detectable group, can be prepared. Synthetic derivatives with desirable properties may also be included in the corresponding polypeptides. All such derivatives and fragments of the above identified genes and gene products showing at least part of the biological activity of the naturally occurring sequences or which are still suitable to be used, for example, as probes for, e.g. identification of homologous genes or gene products, are included within the scope of the present invention.

Having herein provided the nucleotide sequences of various genes functionally involved in cell division and proliferation, it will be appreciated that automated techniques of gene synthesis and/or amplification may be used to isolate said nucleic acid molecules in vitro. Because of the length of some coding sequences, application of automated synthesis may require staged gene construction, in which regions of the gene up to about 300 nucleotides in length are synthesized individually and then ligated in correct succession for final assembly. Individually sythesized gene regions can be amplified prior to assembly, using polymerase chain reaction (PCR) technology. The technique of PCR amplification may also be used to directly generate all or part of the final genes/nucleic acid molecules. In this case, primers are synthesized which will be able to prime the PCR amplification of the final product, either in one piece or in several pieces that may be ligated together. For this purpose, either cDNA or genomic DNA may be used as the template for the PCR amplification. The cDNA template may be derived from commercially available or self-constructed cDNA libraries.

In a second aspect, the invention relates to nucleic acid probes comprising a nucleic acid sequence as previously characterized under (a) to (d) which may be a polynucleotide or an oligonucleotide comprising at least 15 nucleotides containing a detectable label.

These nucleic acid probes may be synthesized by use of DNA synthesizers according to standard procedures or, preferably for long sequences, by use of PCR technology with a selected template sequence and selected primers. In the use of the nucleotide sequences as probes, the particular probe may be labeled with any suitable label known to those skilled in the art, including radioactive and non-radioactive labels. Typical radioactive labels include $^{32}$P, $^{125}$I, $^{35}$S, or the like. A probe labeled with a radioactive isotope can be constructed from a DNA template by a conventional nick translation reaction using a DNase and DNA polymerase. Non-radioactive labels include, for example, ligands such as biotin or thyroxin, or various luminescent or fluorescent compounds. The probe may also be labeled at both ends with different types of labels, for example with an isotopic label at one end and a biotin label at the other end. The labeled probe and sample can then be combined in a hybridization buffer solution and held at an appropriate temperature until annealing occurs.

The invention also includes an assay kit comprising either an isolated nucleic acid molecule as defined above or a fragment thereof or a probe as defined above in a suitable container.

Duplex formation and stability depend on substantial complementarity between the two strands of a hybrid and a certain degree of mismatch can be tolerated. Therefore, the nucleic acid molecules and probes of the present invention may include mutations (both single and multiple), deletions, insertions of the above identified sequences, and combinations thereof, as long as said sequence variants still have substantial sequence homology to the original sequence which permits the formation of stable hybrids with the target nucleotide sequence of interest.

The above identified nucleic acid molecules and probes coding for polypeptides functionally involved in cell division and proliferation or a part thereof will have a wide range of useful applications, including their use for identifying homologous, in particular orthologous, genes in the same or different species, their use in screening assays for identification of interacting drugs that inhibit, stimulate or effect cell division or proliferation, their use for developing computational models, structural models or other models for evaluating drug binding and efficacy, and their diagnostic or therapeutic use for detection or treatment of diseases associated with anomalous and/or excessive cell division or proliferation, in particular neoplastic diseases, including both solid tumors and hemopoietic cancers, or coronary restenosis. Exemplary neoplastic diseases include carcinomas, such as adenocarcinomas and melanomas; mesodermal tumors, such as neuroblastomas and retinoblastomas; sarcomas and various leukemias; and lymphomas. Of particular interest are tumors of the breast, ovaries, gastrointestinal tract, liver, lung, thyroid glands, prostrate gland, brain, pancreas, urinary tract, and salivary glands. Still more specific, tumors of the breast, ovaries, lung, colon, and lymphomas are contemplated.

In a third aspect, the present invention relates to the use of the above identified nucleic acid molecules and probes for diagnostic purposes. This diagnostic use of the above identified nucleic acid molecules and probes may include, but is not limited to the quantitative detection of the expression of said target genes in biological probes (preferably, but not limited to cell extracts, body fluids, etc.), particularly by quantitative hybridization to the endogenous nucleic acid molecules comprising the above-characterized nucleic acid sequences (particularly cDNA, RNA). An annormal and/or excessive expression of said target genes involved in cell division may be diagnosed that way.

In a forth aspect, the present invention relates to the use of the above identified nucleic acid molecules, probes or their corresponding polypeptides for therapeutical purposes.

This therapeutical use of the above identified nucleic acid molecules, probes or their corresponding polypeptides may include, but is not limited to the use of said nucleic acid molecules and their corresponding polypeptides for direct or indirect inhibition of the expression of said target genes and/or for inhibition of the function of said target genes. Particularly gene therapy vectors, e.g. viruses, or naked or encapsulated DNA or RNA (e.g. an antisense nucleotide sequence) with the above-identified sequences might be suitable for the introduction into the body of a subject suffering from a proliferative disease or from a disease affecting cell division for therapeutical purposes.

A particularly preferred therapeutical use of the above identified nucleic acid molecules or probes relates to their use in a therapeutical application of the RNAi technique, particularly in humans or in human cells.

Double-stranded RNA oligonucleotides effect silencing of the expression of gene(s) which are highly homologous to either of the RNA strands in the duplex. Recent discoveries reveal that this effect, called RNA interference (RNAi), that had been originally discovered in *C. elegans*, can also be observed in cells, particularly in human cells. Therefore the invention further comprises the use of double-stranded RNA oligonucleotides with the above identified nucleotide sequences (as stated in a) to d)), preferably with a length of at least 15 nucleotides (nt), more preferably with a length of at least 20 nt, for therapeutical silencing of the expression of genes involved in cell division or proliferation in cells ot other species, particularly in human cells. This therapeutical use particularly applies to cells of an individual that suffers from a disease associated with anormalous and/or excessive cell division or proliferation, particularly a coronary restinosis or a neoplastic disease selected from the group consisting of lymphoma, lung cancer, colon cancer, ovarian cancer and breast cancer.

In a fifth aspect, the invention further comprises a nucleic acid construct or a recombinant vector having incorporated the nucleic acid molecules as defined in (a) to (d) or a fragment thereof.

"Nucleic acid construct" is defined herein as any nucleic acid molecule, either single- or double-stranded, in which nucleic acid sequences are combined and juxtaposed in a manner which will not occur naturally. The vector may be any vector which can be conveniently subjected to recombinant DNA procedures. The choice of the vector will usually depend on the host cell into which it is to be introduced. The vector may be an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the nucleic acid molecule as defined in (a) to (d) or a fragment thereof is operably linked to heterologous or homologous control sequences. The term "control sequences" is defined herein to include all components which are necessary or advantageous for expression of the coding nucleic acid sequence. Such control sequences include, but are not limited to, a promoter, a ribosome binding site, translation initiation and termination signals and, optionally, a repressor gene or various activator genes. Control sequences are referred to as "homologous" if they are naturally linked to the coding nucleic acid sequence of interest and referred to as "heterologous" if this is not the case. The term "operably linked" indicates that the sequences are arranged so that they function in concert for their intended purpose, i.e. expression of the desired protein.

The promoter may be any DNA sequence which shows transcriptional activity in the host cell of choice and may be derived from genes encoding proteins either homologous or heterologous to the host cell.

Examples of suitable promoters for directing the transcription in a bacterial host are, e.g., the phage Lambda $P_R$ or $P_L$ promoters, the lac, tip or tac promoters of *E. coli*, the promoter of the *Bacillus subtilis* alkaline protease gene or the *Bacillus licheniformis* alpha-amylase gene.

Examples of suitable promoters for directing the transcription in mammalian cells are, e.g., the SV40 promoter (Subramani et al., *Mol. Cell. Biol.* 1 (1981), 854-864), the MT-1 (metallothionein gene) promoter (Palmiter et al., *Science* 222 (1983), 809-814) or the adenovirus 2 major late promoter.

Examples of suitable promoters for use in insect cells are, e.g., the polyhedrin promoter (Vasuvedan et al., *Febs. Lett* 311, (1992), 7-11), the Autographa californica polyhedrosis basic protein promoter (EP 397 485), or the baculovirus immediate early gene 1 promoter (U.S. Pat. No. 5,155,037, U.S. Pat. No. 5,162,222).

Examples of suitable promoters for use in yeast cells include promoters from yeast glycolytic genes (Hitzeman et al., *J. Biol. Chem.* 255 (1980), 1203-12080; Alber and Kawasaki, *J. Mol. Appl. Gen.* 1 (1982), 419-434) and the ADH2-4c promoter (Russell et al., *Nature* 304 (1983), 652-654).

The coding sequence may, if necessary, be operably linked to a suitable terminator, such as the human growth hormone terminator (Palmiter et al., *Science* 222, 809-814 (1983)), or a polyadenylation sequence. Also, to permit secretion of the expressed protein, a signal sequence may precede the coding sequence.

Further, the vector may comprise a DNA sequence enabling the vector to replicate in the host cell in question. Examples of such sequences are the origins of replication of the plasmids pUC19, pACYC177, pUB110, pE194, pAMB1 and pIJ702. Another example of such a sequence (when the host cell is a mammalian cell) is the SV40 origin of replication. When the host cell is a yeast cell, suitable sequences enabling the vector to replicate are the yeast plasmid 2μ replication genes REP 1-3 and origin of replication.

The vector may also comprise a selectable marker, e.g. a gene coding for a product which complements a defect in the host cell, such as the gene coding for dihydrofolate reductase (DHFR) or a gene which confers resistance to a drug, e.g. ampicillin, kanamycin, tetracyclin, chloramphenicol, neomycin or hygromycin.

A number of vectors suitable for expression in prokaryotic or eukaryotic cells are known in the art and several of them are commercially available. Some commercially available mammalian expression vectors which may be suitable include, but are not limited to, pMC1neo (Stratagene), pXT1 (Stratagene), pSG5 (Stratagene), pcDNAI (Invitrogen), EBO-pSV2-neo (ATCC 37593), pBPV-1(8-2) (ATCC 37110), pSV2-dhfr (ATCC 37146).

In a sixth aspect, the invention comprises host cells into which the nucleic acid construct or the recombinant vector is introduced. These host cells may be prokaryotic or eukaryotic, including, but not limited to, bacteria, fungal cells, including yeast and filamentous fungi, mammalian cells, including, but not limited to, cell lines of human, bovine, porcine, monkey and rodent origin, and insect cells including, but not limited to, drosophila derived cell lines.

The selection of an appropriate host cell will be dependent on a number of factors recognized by the art. These include, e.g., compatibility with the chosen vector, toxicity of the (co)products, ease of recovery of the desired protein or polypeptide, expression characteristics, biosafety and costs.

Examples of suitable prokaryotic cells are gram positive bacteria such as *Bacillus subtilis, Bacillus licheniformis, Bacillus brevis, Stieptomyces lividans* etc. or gram negative bacteria such as *E. coli.*

The yeast host cell may be selected from a species of *Saccharomyces* or *Schizosaccharomyces*, e.g. *Saccharomyces cerevisiae*. Useful filamentous fungi may be selected from a species of *Aspergillus*, e.g. *Aspergillus oiyzae* or *Aspergillus niger.*

Cell lines derived from mammalian species which may be suitable and which are commercially available include, but are not limited to, COS-1 (ATCC CRL 1650) COS-7 (ATCC CRL 1651), CHO-K1 (ATCC CCL 61), 3T3 (ATCCL 92), NIH/3T3 (ATCC CRL 1658), HeLa (ATCCL 2), and MRC-5 (ATCC CCL 171).

The recombinant vector may be introduced into the host cells according to any one of a number of techniques including, but not limited to, transformation, transfection, protoplast fusion, and electroporation.

The recombinant host cells are then cultivated in a suitable nutrient medium under conditions permitting the expression of the protein of interest. The medium used to cultivate the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

Identification of the heterologous polypeptide expressing host cell clones may be done by several means, including, but not limited to, immunological reactivity with specific antibodies.

In a seventh aspect, the invention is related to a method for producing a polypeptide functionally involved in cell division and proliferation or a fragment thereof in a host cell comprising the steps
(i) transferring the expression vector with an operably linked nucleic acid molecule as defined in (a) to (d) into a suitable host cell, and
(ii) cultivating the host cells of step (i) under conditions which will permit the expression of said polypeptide or fragment thereof and
(iii) optionally, secretion of the expressed polypeptide into the culture medium.

In an eigth aspect, the invention comprises a polypeptide functionally involved in cell division and proliferation or a fragment thereof comprising an amino acid sequence selected from the group consisting of:
(a) the amino acid sequences depicted in SEQ ID NO. 8, 9, 10, 11 and 13 and fragments thereof,
(b) amino acid sequences which exhibit a sequence identity with the sequences of (a) of at least 25% over 100 residues, preferably of at least 30% over 100 residues, more preferably of at least 35% over 100 residues and most preferably of at least 40% over a 100 residues and/or which are detectable in a computer aided search using the BLAST sequence analysis programs with an e-value of at most $10^{-30}$, preferably with an e-value of at most $10^{-35}$ and most preferably with an e-value of at most $10^{-40}$,
(c) amino acid sequences encoded by a nucleic acid molecule that is capable of hybridizing with the nucleic acid sequences of (a) or (b) or encoded by a nucleic acid molecule that is degenerate as a result of the genetic code to any of the sequences as defined in (a) or (b).

The heterologous polypeptide may also be a fusion polypeptide in which another polypeptide is fused at the N-terminus or the C-terminus of the polypeptide of interest or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art and include ligating the coding sequences so that they are in frame and the expression of the fusion polypeptide is under control of the same promotor(s) and terminator.

Expression of the polypeptides of interest may also be performed using in vitro produced synthetic mRNA. Synthetic mRNA can be efficiently translated in various cell-free systems, including but not limited to, wheat germ extracts and reticulocyte extracts, as well as efficiently translated in cell based systems including, but not limited to, microinjection into frog oocytes, preferably *Xenopus oocytes.*

In a ninth aspect, the invention involves antibodies against the above identified polypeptides and against immunogenic fragments thereof. The term "antibody" as used herein includes both polyclonal and monoclonal antibodies, as well as fragments thereof, such as Fv, Fab and F(ab)$_2$ fragments that are capable of binding antigen or hapten. The present invention also contemplates "humanized" hybrid antibodies wherein amino acid sequences of a non-human donor antibody exhibiting a desired antigen-specifity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art (see e.g. WO 89/09622; WO 94/11509; Couto, *Hybridoma* 13 (1994), 215-219; Presta, *Cancer Research* 57 (1997), 4593-4599). The antibodies of the present invention will have a wide range of useful applications, including their use for affinity purification of the corresponding immunogenic (poly)peptides, their use for the preparation of anti-idiotypic antibodies, as well as their use as specific binding agents in various assays, e.g. diagnostic or drug-screening assays, or in a method for treatment of diseases associated with anomalous and/or excessive cell division or proliferation as exemplified above. Specifically, said antibodies or suitable fragments thereof, particularly in humanized form, may be used as therapeutic agents in a method for treating cancer and other diseases associated with anomalous and/or excessive cell division or proliferation as exemplified above. Also, antibodies may be raised to the most characteristic parts of the above identified polypeptides and subsequently be used to identify structurally and/or functionally related polypeptides from other sources as well as mutations and derivatives of the above identified polypeptides.

To raise antibodies against the polypeptides of the present invention, there may be used as an immunogen either the intact polypeptide or an immunogenic fragment thereof, produced in a suitable host cell as described above or by standard peptide synthesis techniques.

Polyclonal antibodies are raised by immunizing animals, such as mice, rats, guinea pigs, rabbits, goats, sheep, horses etc., with an appropriate concentration of the polypeptide or peptide fragment of interest either with or without an immune adjuvant.

Acceptable immune adjuvants include, but are not limited to, Freund's complete adjuvant, Freund's incomplete adjuvant, alum-precipitate, water-in-oil-emulsion containing *Corynebacterium parvum* and tRNA.

In a typical immunization protocol each animal receives between about 0,1 µg and about 1000 µg of the immunogen at multiple sites either subcutaneously (SC), intraperitoneally (IP), intradermally or in any combination thereof in an initial immunization. The animals may or may not receive booster injections following the initial injection. Those animals receiving booster injections are generally given an equal amount of the immunogen in Freund's incomplete adjuvant by the same route at intervals of about three or four weeks until maximal titers are obtained. At about 7-14 days after each booster immunization or about weekly after a single immunization, the animals are bled, the serum collected, and aliquots are stored at about −20° C.

Monoclonal antibodies which are reactive with the polypeptide or peptide fragment of interest are prepared using basically the technique of Kohler and Milstein, Nature 256: 495-497 (1975). First, animals, e.g. Balb/c mice, are immunized using a protocol similar to that described above. Lymphocytes from antibody-positive animals, preferably splenocytes, are obtained by removing spleens from immunized animals by standard procedures known in the art. Hybridoma cells are produced by mixing the splenocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0. Fused hybridoma cells are selected by growth in a selection medium and are screened for antibody production. Positive hybridomas may be grown and injected into, e.g., pristane-primed Balb/c mice for ascites production. Ascites fluid is collected about 1-2 weeks after cell transfer and the monoclonal antibodies are purified by techniques known in the art. Alternatively, in vitro production of monoclonal antibodies (mAb) is possible by cultivating the hybridomas in a suitable medium, e.g. DMEM with fetal calf serum, and recovering the mAb by techniques known in the art.

Recovered antibody can then be coupled covalently to a detectable label, such as a radiolabel, enzyme label, luminescent label, fluorescent label or the like, using linker technology established for this purpose.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay techniques. Similar assays may be used to detect the presence of the above identified polypeptides or fragments thereof in body fluids or tissue and cell extracts.

Assay kits for performing the various assays mentioned in the present application may comprise suitable isolated nucleic acid or amino acid sequences of the above identified genes or gene products, labelled or unlabelled, and/or specific ligands (e.g. antibodies) thereto and auxiliary reagents as appropriate and known in the art. The assays may be liquid phase assays as well as solid phase assays (i.e. with one or more reagents immobilized on a support).

Unless otherwise specified, the manipulations of nucleic acids and polypeptides/-proteins can be performed using standard methods of molecular biology and immunology (see, e.g. Maniatis et al. (1989), Molecular cloning: A laboratory manual, Cold Spring Harbor Lab., Cold Spring Harbor, N.Y.; Ausubel, F. M. et al. (eds.) "Current protocols in Molecular Biology". John Wiley and Sons, 1995; Tijssen, P., Practice and Theory of Enzyme Immunoassays, Elsevier Press, Amsterdam, Oxford, N.Y., 1985).

The invention further includes an assay kit comprising either the polypeptide as defined above or a fragment thereof or an antibody against said polypeptides as defined above or against immunogenic fragments thereof.

These recombinant polypeptides or fragments thereof as well as antibodies against those polypeptides or immunogenic fragments thereof will have a wide range of useful applications, including their use in screening assays for interacting drugs that inhibit, stimulate or effect the cell division or proliferation, their use for developing computational models, structural models or other models for evaluating drug binding and efficacy, and their use in a method for diagnosis or treatment of diseases associated with anomalous and/or excessive cell division or proliferation, in particular neoplastic diseases, including both solid tumors and hemopoietic cancers, or coronary restenosis. Exemplary neoplastic diseases include carcinomas, such as adenocarcinomas and melanomas; mesodermal tumors, such as neuroblastomas and retinoblastomas; sarcomas and various leukemias; and lymphomas. Of particular interest are tumors of the breast, ovaries, gastrointestinal tract, liver, lung, thyroid glands, prostate gland, brain, pancreas, urinary tract, and salivary glands. Still more specific, tumors of the breast, ovaries, lung, colon, and lymphomas are contemplated.

Therefore in a tenth aspect, the present invention explicitly includes the use of polypeptides as defined above or fragments thereof or of antibodies against said polypeptides or immunogenic fragments thereof in a screening assay for interacting drugs that inhibit, stimulate or effect the cell division or proliferation.

Such a screening assay for interacting drugs may particularly comprise, but is not limited to the following steps:
1. recombinant expression of said polypeptide or of an appropriate derivative thereof
2. isolation and optionally purification of the recombinantly expressed polypeptide or of its derivative, in particular by affinity chromatography
3. optionally labelling of the chemical compounds that are tested to interact with said polypeptide or its derivative and/or labelling of the recombinantly expressed polypeptide
4. immobilization of the recombinantly expressed polypeptide or of its derivative to a solid phase
5. binding of a potential interaction partner or a variety thereof to the immobilized polypeptide or its derivative
6. optionally one or more washing steps
7. detection and/or quantification of the interaction, in particular by monitoring the amount of label remaining associated with the solid phase over background levels.

Step 1 includes the recombinant expression of the above identified polypeptide or of its derivative from a suitable expression system, in particular from cell-free translation, bacterial expression, or baculusvirus-based expression in insect cells.

Step 2 comprises the isolation and optionally the subsequent purification of said recombinantly expressed polypeptides with appropriate biochemical techniques that are familiar to a person skilled in the art.

Alternatively, these screening assays may also include the expression of derivatives of the above identified polypeptides which comprises the expression of said polypeptides as a fusion protein or as a modified protein, in particular as a GST-fusion protein or as a protein bearing a so called "tag"-sequence. These "tags"-sequences consist of short nucleotide sequences that are ligated 'in frame' either to the N- or to the C-terminal end of the coding region of said target gene. One of the most common tags that are used to label recombinantly expressed genes is the poly-Histidine-tag which encodes a homopolypeptide consisting merely of histidines. In this context the term "polypeptide" does not merely comprise polypeptides with the nucleic acid sequences of SEQ ID No. 1 bis 7, their naturally occuring homologues, preferably orthologues, more preferably human orthologues, in particular the RP42 gene (SEQ ID No. 12), but also derivatives of these polypeptides, in particular fusion proteins or polypeptides comprising a tag-sequence.

These polypeptides, particularly those labelled by an appropriate tag-sequence (for instance a His-tag) or by GST, may be purified by standard affinity chromatography protocols, in particular by using chromatography resins linked to anti-His-tag-antibodies or to anti-GST-antibodies which are both commercially available. Alternatively to the use of anti-tag- or anti-GST-antibodies or other 'label-specific' antibodies the purification may also involve the use of antibodies against said polypeptides. Screening assays that involve a purification step of the recombinantly expressed target genes as described above (step 2) are preferred embodiments of this aspect of the invention.

In a third—optional—step the compounds tested for interaction may be labelled by incorporation of radioactive isotopes or by reaction with luminescent or fluorescent compounds. Alternatively or additionally also the recombinantly expressed polypeptide may be labelled.

In a forth step the recombinantly expressed polypeptide is immobilized to a solid phase, particularly (but not limited) to a chromatography resin. The coupling to the solid phase is thereby preferably established by the generation of covalent bonds.

In a fifth step a candidate chemical compound that might be a potential interaction partner of the said recombinant polypeptide or a complex variety thereof (particularly a drug library) is brought into contact with the immobilized polypeptide.

In a sixth—optional—step one or several washing steps may be performed. As a result just compounds that strongly interact with the immobilized polypeptide remain bound to the solid (immobilized) phase.

In step 7 the interaction between the polypeptide and the specific compound is detected, in particular by monitoring the amount of label remaining associated with the solid phase over background levels.

BRIEF DESCRIPTION OF THE DRAWINGS

FIG. 5 shows a multiple sequence alignment of the H38K22.2a family. Herein, the amino acid sequences of the two C. elegans splice variants H38K22.2a (SEQ ID NO: 8) and H38K22.2b (SEQ ID NO: 9) are compared to the amino acid sequences of their orthologues in Drosophila (CG7427) (SEQ ID NO: 10), in mouse (AAF04863) (SEQ ID NO: 11)and in homo sapiens (AAH09478) (SEQ ID NO: 13).

Figure 1:
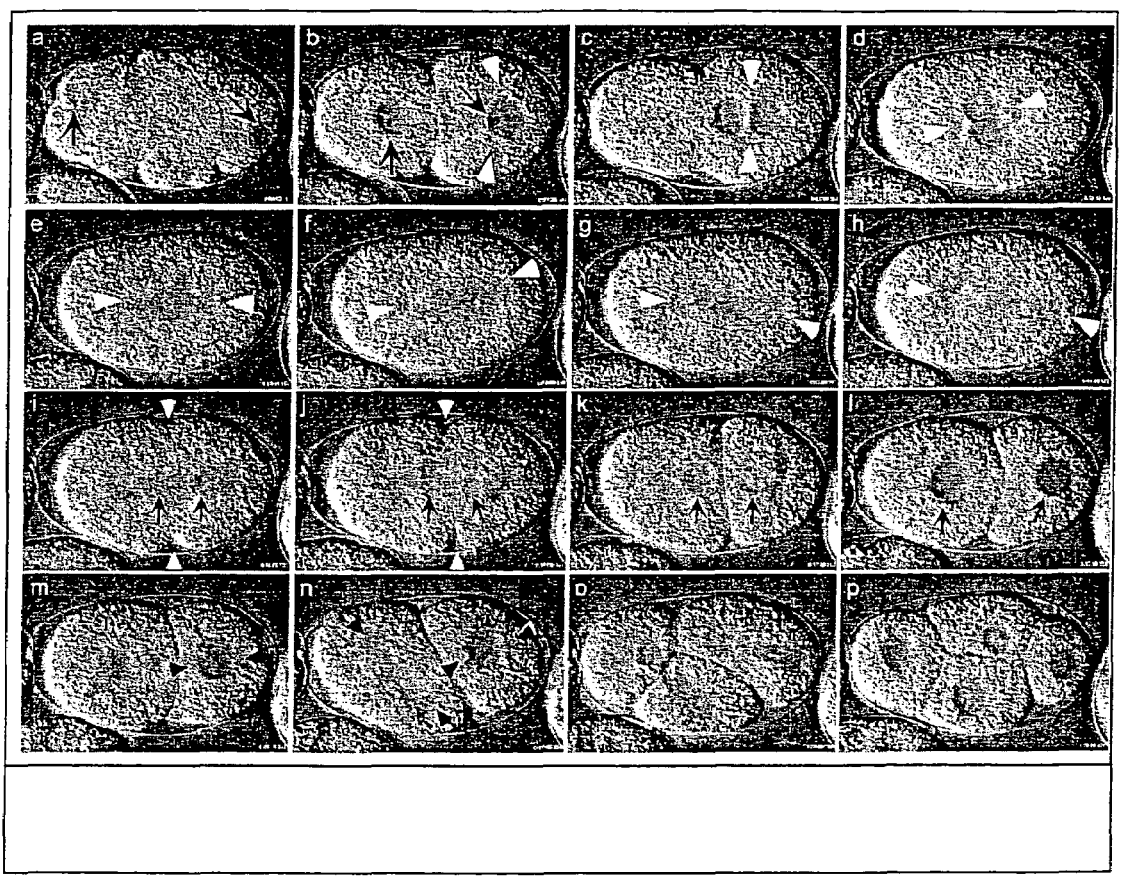
FIG. 1 shows DIC microscopy images taken from time-lapse recording of the first two rounds of embryonic cell division in wild type C. elegans.

The "statistics" refer to values that characterize the grade of homology between the individual sequences, as the e-value, the sequence identities and the conservatively changed residues (positives).

DESCRIPTION OF THE SEQUENCE PROTOCOL

SEQ ID NO. 1 shows the unspliced DNA sequence common to both isoforms a and b of the C. elegans gene H38K22.2 (3104 bp).

SEQ ID NO. 2 shows the spliced DNA sequence of the C. elegans gene H38K22.2a isoform (1011 bp).

SEQ ID NO. 3 shows the spliced DNA sequence of the C. elegans gene H38K22.2b isoform (852 bp).

SEQ ID NO. 4 shows the unspliced DNA sequence of the C. elegans gene C02F5.1 (3308 bp).

SEQ ID NO. 5 shows the spliced DNA sequence of the *C. elegans* gene C02F5.1 (3033 bp).

SEQ ID NO. 6 shows the unspliced DNA sequence of the *C. elegans* gene F10E9.8 (7097 bp).

SEQ ID NO. 7 shows the spliced DNA sequence of the *C. elegans* gene F10E9.8 (3624 bp).

SEQ ID NO. 8 shows the deduced amino acid sequence of the *C. elegans* gene H38K22.2a isoform (336 aa).

SEQ ID NO. 9 shows the deduced amino acid sequence of the *C. elegans* gene H38K22.2b isoform (283 aa).

SEQ ID NO. 10 shows the deduced amino acid sequence of the *C. elegans* gene C02F5.1 (1010 aa).

SEQ ID NO. 11 shows the deduced amino acid sequence of the *C. elegans* gene F10E9.8 (1207 aa).

SEQ ID NO. 12 shows the cDNA sequence of a human orthologue of H38K22.2 (780 bp).

SEQ ID NO. 13 shows the deduced amino acid sequence of a human orthologue of H38K22.2 (260 aa).

The following examples illustrate the present invention without, however, limiting the same thereto.

EXAMPLE 1

Generation of dsRNA Molecules for RNAi Experiments

First, oligonucleotide primer pair sequences were selected to amplify portions of the gene of interest's coding region using standard PCR techniques. Primer pairs were chosen to yield PCR products containing at least 500 bases of coding sequence, or a maximum of coding bases for genes smaller than 500 bases. In order to permit the subsequent use of the PCR product as a template for in vitro RNA transcription reactions from both DNA strands, the T7 polymerase promoter sequence "TAATACGACTCACTATAGG" (SEQ ID NO:15) was added to the 5' end of forward primers, and the T3 polymerase promoter sequence "AATTAACCCTCACTAAAGG" (SEQ ID NO:16) was added to the 5' end of reverse primers. The synthesis of oligonucleotide primers was completed by a commercial supplier (Sigma-Genosys, UK or MWG-Biotech, Germany).

PCR reactions were performed in a volume of 50 µl, with Taq polymerase using 0.8 µM primers and approximately 0.1 µg of wild-type (N2 strain) genomic DNA template. The PCR products were EtOH precipitated, washed with 70% EtOH and resuspended in 7.0 µl TE. 1.0 µl of the PCR reaction was pipetted into each of two fresh tubes for 5 µl transcription reactions using T3 and T7 RNA polymerases. The separate T3 and T7 transcription reactions were performed according to the manufacturer's instructions (Ambion, Megascript kit), each diluted to 50 µl with RNase-free water and then combined. The mixed RNA was purified using RNeasy kits according to the manufacturer's instructions (Qiagen), and eluted into a total of 130 µl of RNase-free H$_2$O. 50 µl of this was mixed with 10 µl 6×injection buffer (40 mM KPO$_4$ pH 7.5, 6 mM potassium citrate, pH 7.5, 4% PEG 6000). The RNA was annealed by heating at 68° C. for 10 min, and at 37° C. for 30 min. Concentration of the final dsRNAs were measured to be in the range of 0.1-0.3 µg/µl. The products of the PCR reaction, of the T3 and T7 transcription reactions, as well as the dsRNA species were run on 1% agarose gels to be examined for quality control purposes. Success of double stranding was assessed by scoring shift in gel mobility with respect to single stranded RNA, when run on non-denaturing gels.

EXAMPLE 2

Injections of dsRNA and Phenotypic Assays dsRNAs were injected bilaterally into the syncitial portion of both gonads of wild-type (N2 strain) young adult hermaphrodites, and the animals incubated at 20° C. for 24 hrs. Embryos were then dissected out from the injected animals and analyzed by time-lapse differential interference contrast videomicroscopy for potential defects in cell division processes, capturing 1 image every 5 seconds, as previously described (Gönczy et al., Dissection of cell division processes in the one cell stage *Caenorhabditis elegans* embryo by mutational analysis. *J Cell Biol* 144, 927-946 (1999)). For each experiment, embryos from at least 3 different injected worms were filmed in this manner, from shortly after fertilization until the four cell stage. Embryos from 2 additional injected worms were also recorded via still images, thus yielding phenotypic documentation for at least 5 injected worms in each experiment.

In some cases, embryos exhibited acute sensitivity to osmotic changes, as evidenced by their loss of structural integrity during the dissection of the injected animals. In order to overcome this limitation, injected animals were not dissected, but rather, anaesthetized for 10 min in M9 medium containing 0.1% tricaine and 0.01% tetramisole, and mounted intact on an agarose pad to observe the F1 embryogenesis in utero (Kirby et al., Dev. Biol. 142, 203-215 (1990)). The resolution achieved by viewing through the body wall does not equal that achieved by observing dissected embryos, and only limited phenotypic analysis was conducted in these cases.

Three injected animals were also transferred to a fresh plate 24 hrs after injection of dsRNA, and left at 20° C. Two days later, the plate was checked with a stereomicroscope (20-40×total magnification) for the presence of F1 larvae (L2's-L4's), as well as their developmental stage. Two days after that, the plate was inspected again for the presence of F1 adults, as well as their overall body morphology and the presence of F2 progeny.

EXAMPLE 3

Characterization of the *C. elegans* Gene H38K22.2

Two dsRNAs, "300C3" and "340G12", were designed and used to specifically silence the expression of the *C. elegans* gene H38K22.2 by RNAi, thereby testing its functional involvement in the first 2 rounds of embryonic cell division in this metazoan species. The dsRNAs were synthesized in vitro from PCR-amplified wild type genomic DNA fragments of the H38K22.2 gene. For the PCR, two sets of primer pairs were used: "TCAATCAGTATGTCGACCC" (SEQ ID NO: 17) with "GGAAGAAATTGGGGAAACA" (SEQ ID NO: 18) as forward and reverse primers, respectively, to generate dsRNA "300C3", and "ATCGAGCGCCTCTTCAATC" (SEQ ID NO: 19) with "TGGTGTCTCCATTTGCTGA" (SEQ ID NO: 20) as forward and reverse primers, respectively, to generate dsRNA "340G12". The dsRNAs were purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilisation, while the female pronucleus is completing its meiotic divisions, until the 4 cell stage, ~30 minutes later.

In the F1 progeny of control worms that were either not injected, or injected with irrelevant dsRNA, the cellular events of the first two rounds of embryonic cell division were found to exhibit very limited variability, as observed by DIC microscopy. All processes that were examined and scored for the possibility of phenotypic deviations are listed and illustrated in FIG. 1. Briefly, the antero-posterior polarity of the embryo is initially determined by the position of the male pronucleus at the cortex, shortly after entry into the egg (right arrow in FIG. 1a). This is accompanied by a clear, coordinated flow of yolk granules through the central portion of the cytoplasm along the embryo's longitudinal axis towards the male pronucleus, and a concomitant series of cortical waves or ruffles progressing towards the anterior of the embryo (left side in FIG. 1). Shortly thereafter, the male and female pronuclei undergo highly patterned migrations (right and left arrows respectively, in FIG. 1a,b) resulting in their meeting within the posterior half of the embryo (FIG. 1c), followed by a centration and rotation (FIG. 1d) of the pronuclear pair and associated centrosomes (arrowheads in FIGS. 1b-d) to set up the future mitotic spindle along the embryo's longitudinal axis. After synchronous breakdown of the pronuclear envelopes, the clearly bipolar mitotic spindle is initially short (FIG. 1e), but then elongates while exhibiting clear lateral "rocking" movements of the posterior pole (FIGS. 1f-h). These movements are accompanied by a slight posterior displacement of the posterior spindle pole, while the anterior spindle pole remains approximately stationary. This then results in an asymmetric positioning of the spindle during anaphase and telophase, thereby yielding an asymmetric placement of the cytokinetic furrow (arrowheads in FIGS. 1i,j), and generating unequally-sized daughter cells: a smaller posterior P1 blastomere (right cell in FIGS. 1k-o), and larger anterior AB blastomere (left cell in FIGS. 1k-n). While the AB nucleus then migrates directly to the center of the AB cell (left arrow in FIGS. 1k-l), the P1 nucleus typically migrates further towards the posterior of that cell (right arrow in FIGS. 1k-l), before undergoing a pronounced 90° rotation while re-migrating to the anterior P1 cortex with one of its duplicated centrosomes leading (arrowheads in FIG. 1m). This insures that the P1 blastomere then divides along the embryo's longitudinal axis, perpendicular to that of the AB blastomere (FIG. 1n, arrowheads indicate centrosomes). These two divisions occur asynchronously, with P1 lagging 2-3 minutes behind AB (FIGS. 1n-p).

Figure 2:
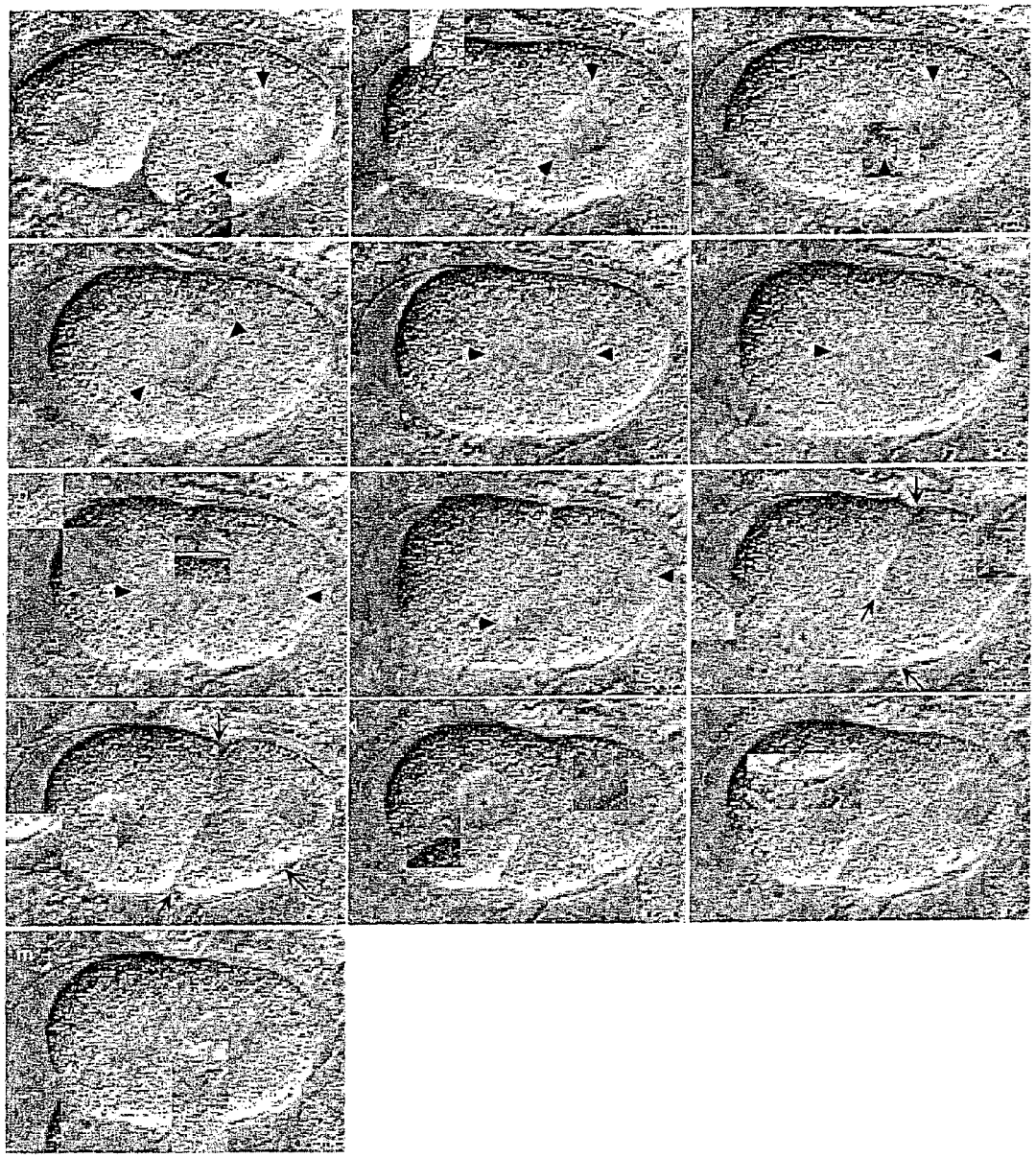
FIG. 2 shows DIC microscopy images taken from time-lapse recording of the first two rounds of embryonic cell division in C. elegans F1 progeny from F0 parent treated with ds RNA "300C3" or "340G12" directed against gene H38K2.2.

In the F1 embryos of worms injected with dsRNAs "300C3" or "340G12", the following highly reproducible phenotypes are observed (FIG. 2). First, although the dynamics of female pronuclear migration appear normal in all cases, its initiation is often somewhat delayed. Meeting and apposition of the two pronuclei also typically exhibits defects in that the female pronucleus gets captured by only one of the two centrosomes associated with the male pronucleus (compare FIGS. 2a-c with FIGS. 1a-c). Although this defect is usually corrected before pronuclear envelope breakdown is completed, subsequent positioning of the mitotic spindle within the embryo often appears defective. Weak manifestation of this phenotype appears as a lack of rocking of the posterior spindle pole during anaphase, while more severe cases show a notable drift of the entire spindle towards the posterior or lateral cortex, reaching the cortex itself and losing its longitudinal alignment completely. In the latter cases, the strongly aberrant spindle position gives rise to inappropriate specification of cleavage furrow formation, leading to anomalous cytokinesis. Even in cases where spindle position appears relatively normal, positioning of the daughter Nucleus-Centrosomes-Complexes (NCCs) typically appears abnormal as soon as anaphase ends and the cleavage furrow ingresses. This is often particularly visible in the AB blastomere, where the NCC, instead of moving directly to the centre of the cell starting at telophase, first migrates anteriorly in close proximity to the lateral cortex before eventually centering (FIGS. 2a-k). This defect is usually accompanied by an apparent absence of interzonal spindle microtubules at telophase and a notable bifurcation or forking of the cytokinetic cleavage furrow (arrows in FIG. 2g), leading to aberrantly-sized daughter blastomeres or even failure of cytokinesis by complete regression of the furrow (FIGS. 2g-m). Nuclear migration and positioning of the P1 nucleus is also aberrant in most cases, resulting in a significant delay—or in some cases, a complete failure—in achieving its expected 900 rotation and association with the anterior cortex. Division of the P1 blastomere is often significantly delayed in such embryos. Finally, defects in female meiotic divisions are also occasionally observed, as evidenced by the presence of multiple female pronuclei, indicating a failure to successfully extrude one or both polar bodies, which could come from cytokinetic defects similar to those noted above.

All observed phenotypes indicate a requirement for H38K22.2 gene function in the microtubule-dependent cellular positioning of NCCs and spindles during mitosis, and possibly meiosis. Since this function is essential to cell cycle progression and cell division throughout metazoans, this gene and any homologues and derivatives thereof represent excellent tools for use in the development of a wide range of therapeutics including anti-proliferative agents. Analysis of the H38K22.2 gene sequence reveals clear orthologues in human (NCBI Accession # AAH09478), mouse (NCBI Accession # AAF04863) and Drosophila (NCBI Accession # CG7427) (see FIG. 5), all of which have had no known functions ascribed to them until now. Based on their extremely high level of sequence conservation at the protein level, it can be concluded that all of these genes most likely encode proteins with equivalent functions in each of their respective species. The 336 residue protein encoded by the H38K22.2 gene isoform "a" exhibits no known structural motifs or consensus domains, according to either SMART or CDD analyses.

EXAMPLE 4

Characterization of the *C. elegans* Gene C02F5.1

A dsRNA, "307C1", was designed and used to specifically silence the expression of the *C. elegans* gene C02F5.1 by RNAi, thereby testing its functional involvement in the first 2 rounds of embryonic cell division in this metazoan species. The dsRNA was synthesized in vitro from a PCR-amplified wild type genomic DNA fragment of the C02F5.1 gene. For the PCR, oligonucleotides with sequences "ATCT-GAAGATCCGTCCACT" (SEQ ID NO: 21) and "ATGCA-CAATGGGTATTTTT" (SEQ ID NO: 22) were used as forward and reverse primers, respectively, to generate dsRNA "307C1" which was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilisation, while the female pronucleus is completing its meiotic divisions, until the 4 cell stage, ~30 minutes later.

In the F1 progeny of control worms that were either not injected, or injected with irrelevant dsRNA, the cellular events of the first two rounds of embryonic cell division were found to exhibit very limited variability, as observed by DIC microscopy. All processes that were examined and scored for the possibility of phenotypic deviations are listed and illustrated in FIG. 1.

Figure 3:
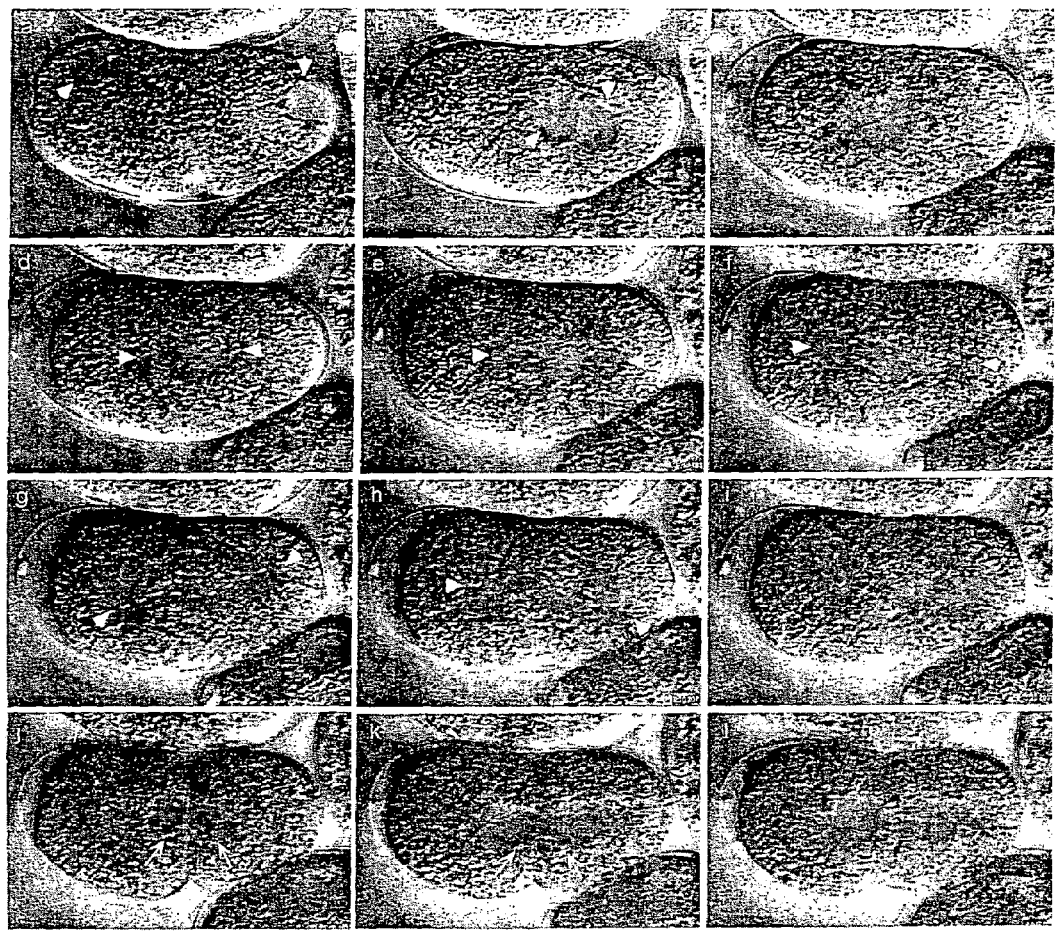
FIG. 3 shows DIC microscopy images taken from time-lapse recording of the first two rounds of embryonic cell division in C. elegans F1 progeny from F0 parent treated with dsRNA "307C1" directed against gene C02F5.1.

F1 embryos from parent worms injected with dsRNA "307C1" are consistently found to exhibit the following phenotypes (FIG. 3). First, all cellular processes that are scorable by DIC microscopy until entry into mitosis are typically indistinguishable from the wild type pattern. These include egg shape and size, yolk granule size and density, yolk granule flows and cortical ruffling, pseudo-cleavage furrow formation and positioning, pronuclear appearance (arrows in FIG. 3a) and migration (FIGS. 3a,b), as well as centration and rotation of pronuclei (FIGS. 3b,c) and associated pair of centrosomes (arrowheads in FIGS. 3b,c). Formation and positioning of the bipolar mitotic spindle also take place normally, but the spindle is most often thinner and less rigid than in wild type, exhibiting aberrant lateral bending during its rocking and elongation at anaphase (FIGS. 3f-i). After completion of cytokinesis, which appears normal, the reforming daughter nuclei are typically tear-shaped, and remain close to the newly-formed cortex for a prolonged period (FIGS. 3a and k). Consistent with the tear shape, the two nuclei remain often physically connected by anomalous chromatin bridges and karyomeres are also typically seen (asterisks in FIGS. 3k and l). This phenotype subsequently results in embryonic lethality in all cases. The absence of defects in pronuclear migration and assembly of the bipolar spindle argue against a role for this gene in more general microtubule functions. The observed defects are consistent with a failure in mitotic chromosome segregation, most likely in the separation of sister chromatids, resulting in the formation of chromatin bridges, which then persist at telophase. The present data therefore indicate an essential requirement for C02F5.1 gene function in mitotic chromosome segregation. Since this function is essential to cell cycle progression and cell division throughout metazoans, this gene and any homologues and derivatives thereof represent excellent tools for use in the development of a wide range of therapeutics including anti-proliferative agents.

Analysis of the C02F5.1 sequence reveals that the encoded 1010 residue protein contains regions predicted to form coiled coil structures, i.e. likely protein-protein interaction domains. Sequence homology analyses using the BLASTp program presently reveal no clearly orthologous sequences in other organisms. However, considering the essential and highly conserved nature of the cellular process in question, functional orthologues of this gene/protein are extremely likely to exist in all metazoans, possibly in all eukaryotes, and will be identified using for example the methodology as outlined in EXAMPLE 6.

EXAMPLE 5

Characterization of the *C. elegans* Gene F10E9.8

Two dsRNAs, "305A12" and "341G5", were designed and used to specifically silence the expression of the *C. elegans* gene F10E9.8 by RNAi, thereby testing its functional involvement in the first 2 rounds of embryonic cell division in this metazoan species. The dsRNAs were synthesized in vitro from PCR-amplified wild type genomic DNA fragments of the F10E9.8 gene. For PCR, two sets of primer pairs were used: "TTCGTCTCGAACACG-TATATCCT" (SEQ ID NO: 23) with "GAAAGAAGAT-GAATCAGGCATTG" (SEQ ID NO: 24) as forward and reverse primers, respectively, to generate dsRNA "305A12", and "CTGCAAAAATTATGACTGTGTCG" (SEQ ID NO: 25) with "AGCATTCAGATTTGGTTGTCC" (SEQ ID NO: 26) as forward and reverse primers, respectively, to generate dsRNA "341G5". The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilisation, while the female pronucleus is completing its meiotic divisions, until the 4 cell stage, ~30 minutes later.

In the F1 progeny of control worms that were either not injected, or injected with irrelevant dsRNA, the cellular events of the first two rounds of embryonic cell division were found to exhibit very limited variability, as observed by DIC microscopy. All processes that were examined and scored for the possibility of phenotypic deviations are listed and illustrated in FIG. 1.

Figure 4:
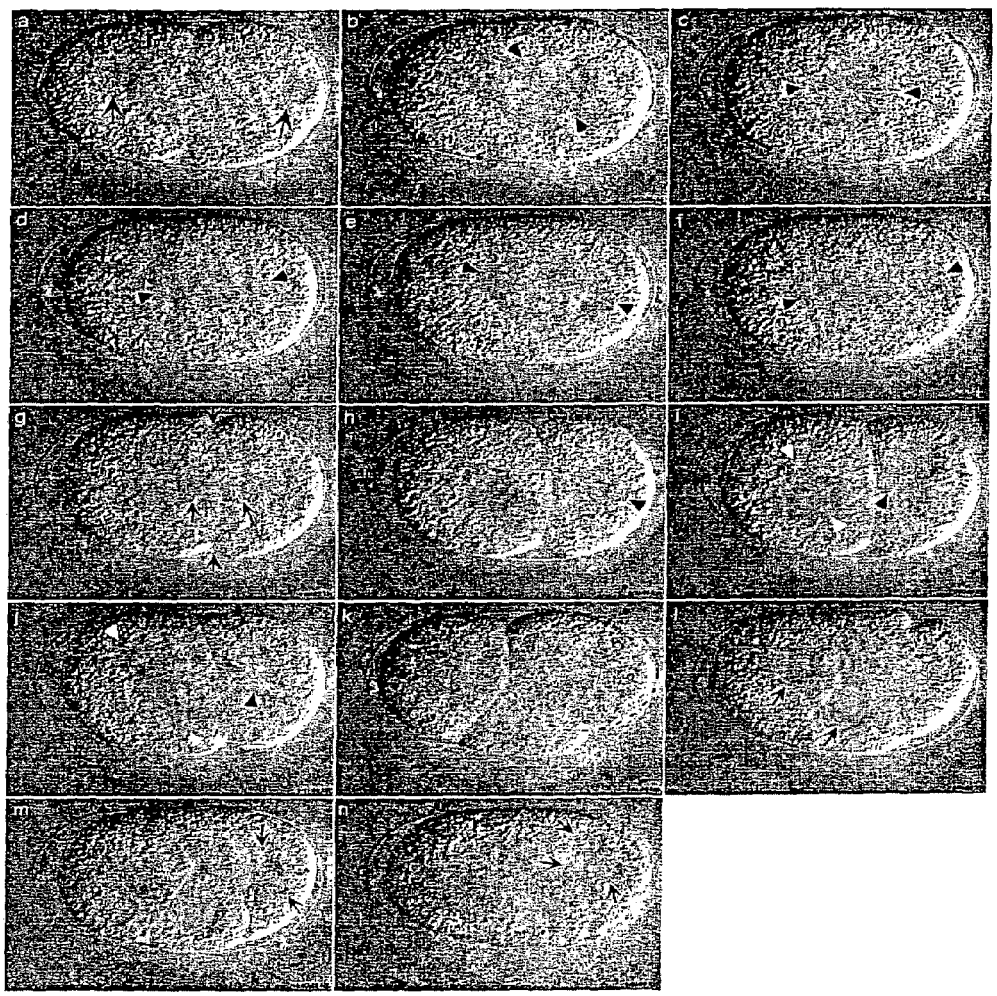
FIG. 4 shows DIC microscopy images taken from time-lapse recording of the first two rounds of embryonic cell division in C. elegans F1 progeny from F0 parent treated with ds RNA "305A12" directed against gene F10E9.8.

In the F1 embryos of worms injected with dsRNAs "305A12" or "341G5", the following highly reproducible phenotypes are observed (FIG. 4). First, all cellular processes that are scorable by DIC microscopy until the 2-cell stage are typically indistinguishable from the wild type pattern. These include egg shape and size, yolk granule size and density, yolk granule flows and cortical ruffling, pseudo-cleavage furrow formation and positioning, pronuclear appearance (arrows in FIG. 4a) and migration (FIGS. 4a,b), as well as centration and rotation of pronuclei (FIGS. 4b,c) and associated pair of centrosomes (arrowheads in FIGS. 4b,c). The first round of division also occurs without any detectable deviations from wild type (FIGS. 4d-h). It should particularly be noted that no defects are observed with respect to size, number or positioning of centrosomes or spindle poles in the single cell embryo (note arrowheads in FIGS. 4b-f). In the two-cell stage embryo, however, although nuclear positioning also remains equivalent to wild type, an apparent failure in centrosome duplication is consistently observed in one of the two blastomeres and sometimes in both. A single perinuclear centrosomal region, as seen by its exclusion of yolk granules (black arrowhead in FIGS. 4h-j), is typically observed instead of the two normally seen both in wild type embryos and in the unaffected blastomere (white arrowheads in FIGS. 4i,j). Despite the apparent failure in centrosome duplication, microtubule-dependent processes continue normally, as illustrated by the successful anterior migration of the P1 nucleus, with its single centrosomal region leading (black arrowhead in FIGS. 4h-j). Upon entering mitosis, as scored by nuclear envelope breakdown, the defective blastomere then fails to generate a bipolar spindle, forming instead a monopolar array of microtubules (dashed circle in FIG. 4k), as evidenced by the radial alignments of yolk granules in that region. Cytokinesis fails to occur in that blastomere, resulting in reformation of multiple, irregularly sized nuclei, known as karyomeres (arrows in FIGS. 4m,n). In contrast, all aspects of cell division occur normally in the neighboring blastomere, resulting in normal daughter cells, each containing a single equal-sized nucleus (arrows in FIG. 4l).

The complete failure in bipolar spindle formation, accompanied by the presence of a single centrosomal region instead of two in the affected two-cell stage blastomere, clearly indicates a requirement for F10E9.8 gene function in the complex process of mitotic spindle assembly. However, the lack of detectable defects in other microtubule-dependent processes including pronuclear migration and spindle function in the single-cell embryo effectively rules out a general microtubule-related function. In view of the maternal nature of the RNAi effect and the fact that the egg inherits its first centrosome paternally, the successful generation of a bipolar spindle in the single-cell embryo further suggests that F10E9.8 function may, in fact, be required for some aspect of centrosome duplication or separation.

Indeed, since sperm development is fully completed within the parent before initiation of the RNAi treatment, it remains unaffected by the injected dsRNA. This results in the donation of an intact "wild type" centrosome from the sperm to the egg at fertilisation. After fertilisation, this already bipartite centrosome (i.e. containing two "replication units", as evidenced by the presence of two centrioles) undergoes one round of duplication, as observed in other systems by the budding of a new centriole barrel from each existing centriole. This is followed by a physical separation of the two centriole pairs and associated pericentriolar material. This process is not dependent on the prior duplication event, and is solely needed to insure the successful formation of the bipolar spindle to be used in the first round of embryonic cell division. It therefore appears that F10E9.8 function is most likely not required for this process.

5. If the first duplication round fails, however, bipolar spindle formation is expected to fail during the second round of division, as seen here. Interestingly, the fact that this failure often occurs only in one of the two blastomeres suggests that in these cases only one of the original centrosome's two "replication units" actually failed in its first round of duplication at the single-cell stage. This observation is consistent with findings from other eukaryotes indicating that one of the two replication units contained within the sperm's centrosome actually comes into the egg already fully equipped for one duplication round, while the other must rely on cytoplasmic factors within the egg to permit its own duplication (Sluder, G., Hinchcliffe EH. Control of centrosome reproduction: the right number at the right time. *Biol. Cell*. 91, 413-27 (1999).

The present findings therefore suggest that the requirement for F10E9.8 function in mitotic spindle assembly most likely results from this gene's essential role in the process of centrosome duplication.

Since the process of spindle assembly is essential to cell cycle progression and cell division throughout metazoans, this gene and any homologues and derivatives thereof represent excellent tools for use in the development of a wide range of therapeutics including antiproliferative agents. Analysis of the F10E9.8 sequence reveals that the encoded 1207 residue protein contains one large region predicted to form coiled coil structures, i.e. likely protein-protein interaction domains, and four predicted transmembrane domains. Sequence homology analyses using the BLASTp program presently reveal no clearly orthologous sequences in other organisms. However, considering the essential and highly conserved nature of the cellular process in question, functional orthologues of this gene/protein are extremely likely to exist in all metazoans, possibly all eukaryotes, and will be identified using for example the following methodology.

EXAMPLE 6

Protocol for Identifying Functional Orthologues in Other Species

The present invention describes genes identified as having essential functions in cell division in the model organism *C. elegans*. The basis for performing research in model organisms is that the newly discovered functions for the genes in *C. elegans* will be conserved in other species including humans. Cell division is highly conserved during evolution and therefore the approach of discovering a gene function in *C. elegans* and using the information to characterise or assign functions for the human orthologue is well justified. There are two themes of conservation of genes during evolution. A gene sequence may be conserved. This means that the DNA nucleotide sequence of the gene is very similar in different species, which in turn suggests that the function of the gene is the same in the different species. As is known to any person skilled in the art, a sequence identity or homology above a particular level defines that two genes in different species code for the same gene product and gene function. Homologous genes are typically identified by performing blast analysis with appropriate software, or by other approaches. For a blast search, an e-value of $10^{-30}$ will extract the significant homologous sequences. Further phylogenetic analysis can be performed to identify which of the extracted sequences are the orthologues.

Therefore the following example for identification of orthologues can be presented. A blast search is performed using the blast sequence analysis programs and an e-value of $10^{-3}$. An alternative parameter can be the percentage of sequence identity. Over 100 residues, a sequence identity of 30% defines a homologous gene. After the blast search is completed, multiple sequence alignment is performed using appropriate software (for example, CLUSTALW) and a neighbour joining phylogenetic tree is generated. Any person skilled in the art can identify the human orthologue from a phylogenetic tree. Essentially, the human sequence that is separated on the tree by a single speciation event or most closely related on the tree is likely to be an orthologue.

The second theme of conservation is that the gene function can be conserved with greater divergence of sequence. In the present invention this theme of conservation is not defined. However, if other genes are discovered to have functions that result in the gene product being identified as the same gene product as those claimed in the present invention then the present claims also apply to such genes.

The invention claimed is:

1. A screening method for interacting drugs that inhibit, stimulate or effect cell division or proliferation comprising the steps of:
    (1) contacting said drug with a polypeptide having the amino acid sequence of SEQ ID NO. 13, and
    (2) determining whether said drug is capable of inhibiting, stimulating or effecting cell division or proliferation.

2. The screening method as claimed in claim 1 comprising the steps:
    (1) recombinantly expressing said polypeptide in a host cell,
    (2) isolating and optionally purifying the recombinantly expressed polypeptide of step 1,
    (3) optionally labelling the drugs that are potential interaction partners and/or labelling the recombinantly expressed polypeptide,
    (4) immobilizing the recombinantly expressed polypeptide to a solid phase,
    (5) binding the potential interaction partner to the polypeptide,
    (6) optionally washing the binding complex of step 5 one or more times, and
    (7) detecting and/or quantifying the interaction, in particular by monitoring the amount of label remaining associated with the solid phase over background levels.

* * * * *

SEQUENCE LISTING

<160> NUMBER OF SEQ ID NOS: 26

<210> SEQ ID NO 1
<211> LENGTH: 3104
<212> TYPE: DNA
<213> ORGANISM: C. elegans

<400> SEQUENCE: 1

```
atgaatcgac tgaagtccga tcaaaaaaca aaggtttgta aacggaaaca agacgatgaa      60
gtggagatga gtgatatgga aactgatcac aaaaagtgta gaaaacaaga aaacagtaaa     120
tttgtgcgtg tgaaaattcc attcgtcatc cattcccgtt tttctctttt tcagcattta     180
tctcgagcaa gttcgagttc tctagctcaa agcactgttc tttctgacat tttcccaag     240
aactacgata atatcgtgag ttgtagcggg aatttcgaaa aaaaaactaa ttttgccaca     300
tcttgctgct tcgtttgtta tttcttgact agacaaattc tagctcatct agaaagctga     360
cttttctcaa aatcgttgcg agacccaaag cagaaaaatg tatcttttt aaatctacgt      420
ggaaacgcgc tccaatatta aatttcgagg ttttcccgcc aaatacctaa cgagacccaa     480
ctttggcgag cagagcgttt tgcccgcgat tttcctgcgt ctcttcaaac aatctaatca     540
ctgctgctgg tttatgaaat atcaattttc ctcatttttt aaagctgagc aatgttttcg     600
ctcaatccta aaattttag tagttctaat tgtgatcaac ggtttcccat ttccgatcga      660
agtcactttt taaattctca cttttattga ttttttcgt tttgaaattc ctgatttctt      720
ccttttagt gataagacat cagttgctga ctgtagagaa agtgtgagaa actgttagtg      780
agagagagaa aacagtttga gaaaatgaaa aatgttttaa ataatgatat cataattatt     840
atttgatacc atttccagct ccggcagttc gtccagtgga ctcaggtcac ggaagctgtg     900
tctctcaact tcctggcaaa agctaattgg aatatcgaat acgcgatgac tctgtatttc     960
gacaatccta atcttttgc tggatcgaca ccacagccga gcgttgatag gtccaatgta     1020
cggcaattgc tgactttggc aactctacag aatgataatg ttctcacaat attttaatt     1080
aaaatttagt tatatttaga ctatagaaaa aatatttgat ttatctgaaa atacatttta    1140
tttcagttgg aataattgga aaagtgctct caaataattg ttttgagcg cttttttaat     1200
tgttccaact gaaatcaaag ccattttcag ataaagcaaa ttttttaaa gtatatcact     1260
aagtttaat tctaaaaaag tattgggaga acatgtcaca ccgactcatt tgttgaatt      1320
gccgacaatt gcagaattta aattaatta tgtaaataaa agtaattttt gtagatcgag     1380
cgcctcttca atcagtatgt cgacccaaag gataaagttg gagaaaaacg aatgggaccc    1440
cacggaatca atcgtttgct cactgatctt ggctatgaag ctactgatcg ccgggttctt    1500
gtgctcgcct ggaagtttac tgcacagaca caatgtgaat tctcgttgga tgaatgggtg    1560
aaaggaatga cagctcttca agcggatact gttcaaaatt tgagacaacg aatcgattcg    1620
attaattcag gactggaatc ggataaggca aaagtacgga aaaaattaaa taactggaat    1680
tatcttccaa acttatttga aagtgggaga gcgaatttgc acttttaag aacaaattca     1740
cgcaaaacac tgtaaattga agttaattga aaattttga tgtaaaatac agagaaaat      1800
tacacacttt tcctcgagga gtacacgggc tgcgtaaatc aacacatagc tttattgttg    1860
gttcacacca cggcagtatg ataatcaaaa aaaaattta attgaaaaat tgaaattaag    1920
atggaggaaa atgttatttc gatctggaaa taatatttat ttttgtgaaa attaataaat    1980
ataattttca gaccgaagga aaattttaat acgtttctat aataattttc gattcaaaaa    2040
tttgaattat cacaattttt aaaaacaaaa aggttctacg atcgtctcat atctaatatc    2100
ttatcagtta cagttccacg agctctacct atttgcttc aactatgcca aatccgccgc     2160
ttgccgcaat ctggatcttg aaactgccat ctgttgctgg gatgttcttt tcggacaacg    2220
atcaacaatt atgactcaat ggatcgattt tctatgggca caggagaacg cggcggcgtc    2280
tcgcctcgct cagaacgtgg gcgcttccaa tgcgaagcaa ttcaaatcgg tgtggatctc    2340
```

```
tcgtgacacg tggaatctct tctgggactt tattcttctg agtaagccag atttgtcgga    2400
ttacgatgat gaaggagcat ggccagtgct tattgatcaa ttcgttgatt attgccgtga    2460
aaatctcaat tatccaaagc caggaaatgc gtcaaatgat cagcaaatgg agacaccaag    2520
ttattattag gacaaacaat tctaaaatcc taaaggttcg tgtttcccca atttcttcct    2580
attttcagag ttataaaata ttgcctggac gcgaaatttt gcttcaaaac tacggtacca    2640
ggtctcggca cgacaaatat tggttaaatg cgaaaatgca cgcgccttca atgggtactg    2700
tagtttcaca cttttcaaaa cgttaatttt tctatgacaa cagataagct ttaaaaaatc    2760
ttgtgaaaaa cttcaaaaaa tcaaagtttt gaaggcgcac atattttaac aaaaaatgtt    2820
tcgtgccgag accggctacc gtattttta tgcgaaattt cgcgtttgtg taatatttt     2880 atattatacc gagaaaactc gacactttaa aggtgtggta gcgaattggg attttatttc    2940
gaaaaatatc ctaaatattc ccaaattcag aaatagcgca aaagaaaccc ggaattttt    3000 attttaattc taatttacaa ctaatagaat tcaaattgtt tcagtatccc atgctcaaga    3060
ctatcttcaa aataacaatt cacaccgccg gaacaaatcg ataa                     3104

<210> SEQ ID NO 2
<211> LENGTH: 1011
<212> TYPE: DNA
<213> ORGANISM: C. elegans

<400> SEQUENCE: 2
atgaatcgac tgaagtccga tcaaaaaaca aagctccggc agttcgtcca gtggactcag      60
gtcacggaag ctgtgtctct caacttcctg gcaaaagcta attggaatat cgaatacgcg     120
atgactctgt atttcgacaa tcctaatctt tttgctggac cgacaccaca gccgagcgtt     180
gataggtcca atatcgagcg cctcttcaat cagtatgtcg acccaaagga taaagttgga    240
gaaaaacgaa tgggacccca cggaatcaat cgtttgctca ctgatcttgg ctatgaagct    300
actgatcgcc gggttcttgt gctcgcctgg aagtttactg cacagacaca atgtgaattc    360
tcgttggatg aatgggtgaa aggaatgaca gctcttcaag cggatactgt tcaaaatttg    420
agacaacgaa tcgattcgat taattcagga ctggaatcgg ataaggcaaa attccacgag    480
ctctacctat ttgccttcaa ctatgccaaa tccgccgctt gccgcaatct ggatcttgaa    540
actgccatct gttgctggga tgttcttttc ggacaacgat caacaattat gactcaatgg    600
atcgattttc tatgggcaca ggagaacgcg cggcgtctc gcctcgctca gaacgtgggc     660
gcttccaatg cgaagcaatt caaatcggtg tggatctctc gtgacacgtg gaatctcttc    720
tgggacttta ttcttctgag taagccagat ttgtcggatt acgatgatga aggagcatgg    780
ccagtgctta ttgatcaatt cgttgattat tgccgtgaaa atctcaatta ccaaagcca     840 ggaaatgcgt caaatgatca gcaaatggag acaccaaaaa tagcgcaaaa gaaacccgga    900
attttttatt ttaattctaa tttacaacta atagaattca aattgtttca gtatcccatg    960
ctcaagacta tcttcaaaat aacaattcac accgccggaa caaatcgata a             1011

<210> SEQ ID NO 3
<211> LENGTH: 852
<212> TYPE: DNA
<213> ORGANISM: C. elegans

<400> SEQUENCE: 3
atgaatcgac tgaagtccga tcaaaaaaca aagatcgagc gcctcttcaa tcagtatgtc      60
```

```
gacccaaagg ataaagttgg agaaaaacga atgggacccc acggaatcaa tcgtttgctc    120
actgatcttg gctatgaagc tactgatcgc cgggttcttg tgctcgcctg gaagtttact    180
gcacagacac aatgtgaatt ctcgttggat gaatgggtga aggaatgac agctcttcaa     240 gcggatactg ttcaaaattt gagacaacga atcgattcga ttaattcagg actggaatcg    300
gataaggcaa aattccacga gctctaccta tttgccttca actatgccaa atccgccgct    360
tgccgcaatc tggatcttga aactgccatc tgttgctggg atgttctttt cggacaacga    420
tcaacaatta tgactcaatg gatcgatttt ctatgggcac aggagaacgc ggcggcgtct    480
cgcctcgctc agaacgtggg cgcttccaat gcgaagcaat caaatcggt gtggatctct     540 cgtgacacgt ggaatctctt ctgggacttt attcttctga gtaagccaga tttgtcggat    600
tacgatgatg aaggagcatg gccagtgctt attgatcaat cgttgatta ttgccgtgaa     660 aatctcaatt atccaaagcc aggaaatgcg tcaaatgatc agcaaatgga gacaccaaaa    720
atagcgcaaa agaaacccgg aattttttat tttaattcta atttacaact aatagaattc    780
aaattgtttc agtatcccat gctcaagact atcttcaaaa taacaattca caccgccgga    840
acaaatcgat aa                                                        852

<210> SEQ ID NO 4
<211> LENGTH: 3308
<212> TYPE: DNA
<213> ORGANISM: C. elegans

<400> SEQUENCE: 4
atgtcgatgg agcctcgtaa gaagcggaac tcgattctca aggtgcggca agccgtcgaa     60
accatcgagg aaaccgtcat gaacagtggg cctagttcca caacaactaa tcgacgagtc    120
agctttcata acgtgaagca tgtcaagtca gttagagtca gtgaataatt tatcaataaa    180
ataattattt caggcagtat gacagggacc atggtaaaat tcttgacgcc acaccagtta    240
aggagaagat tactgacact attggatcag atggtatttt gacgtgagtt ccatcccttta   300 acgtgaaata atgaatacgt aaaaatcttt ttaagaccac gtggcggaaa catggatatt    360
tccgaatctc cggcctgcac gtcctcattt caagtgttcg gcggtggtaa tctcgataaa    420
actatggata tgtctctcga acaactatc aacgagaaca acgaaacggc gagattgttt      480
gaaaccacaa gagatccaac actattatac gaaaagatcg tcgaaaccac aacaaaagtt    540
accgagcgaa ttgttagtat gccactggat gataccttag caatgttcaa tacaacgaat    600
caagaagata aggatatgtc agttgatcgt tcagttcttt tcacgattcc caaagttccg    660
aagcataacg ctacaatgaa tagaactata ccgatggacc tcgatgaatc aaaagcagcg    720
ggcggccagt gcgatgaaac ggtatgttga attaatagaa ggaaccaaat tatcttaatt    780
ttacagatga atgtgttcaa tttcacaaac ttggaagccg ctgaaatgga tacgagtaaa    840
ttagatgaaa ataataccat gaatgctatc cggattccga ttaattcaaa cgtcatgcct    900
gtagacatgg acatcactga acatcacact ttaattgaag aaaagaaaaa tgatacattc    960
gggccaagtc aactgatgga catttcggcg ccacaagttc aagttaatga actttttggcc   1020 attttcaaca gtccgagaga catctgtaat aagggtttgg gtgttcctca gaatctaata   1080
aatatcgcct cgaacgtcgt acctgtggac atggacatca ctgatcaggc cgtattaaac   1140
gcggagaaga aaatgatca attcgagaca agtcagctta tggacatttc tattccgaaa    1200
gttctagtaa atgacactat ggcgatgttc aacagcccga aacacgtcag taagagcagc   1260
atggatctcg agaaaacgat tgaagccgct gacaaatcaa cgaaatacccc gagtatcgca  1320
```

```
gatgaggtgg aagatttaga catggatatg gatatcactg aacaacaacc atgtgaggct   1380
ggtaatcagc agaacgacgg cttgcaactt caaaaggagg atttaatgga catttcggtg   1440
attcgagatt cacctgcagt aaacgacacc atggctgtgt tccagagtcc tgccagagta   1500
aagatcggag cggtaagttt taagcacact ttccaataaa aatgtatttc tttcagaaca   1560
actcgatcat tgattcgcag aaatctatcg tgttcggtga cgaaatgagc attgacgaga   1620
cacaaaatga tggaaccttg acgttgccaa agtcgaatgt agaagtgact acaactaatg   1680
atgtctacac gtctctcgag cggcaagagg aaaatgcttc agaaacgta tccatgataa   1740 acgaatcttc tgttcattcg gaaatcgaca aaaagtcgtt tatgctcatc gaagaagaaa   1800
gggcttttat gcactcctcc atgattgatg tagcacaaaa gttggaagac gatggttcgt   1860
cgaagacgcc agtcatcctt gcttcacagt cagcttctct tgccactaaa gaaccatcag   1920
cccttcacaa ctcgagtgca actctcaaca attcgatgga attggacaac aatactcttc   1980
ttaaaactat gcaaattaca acgtgtgaag acattagcat ggtccatgag tctattgctg   2040
ttgaactgaa cagtaacaaa gagcaggagc aattcggaga tgagactttg cagaaaaatg   2100
gtaaatttcg tttattcaat aactctatta aaagtatgtt ttagatacct cgaatactgg   2160
cgcgaatttc acattccaag gccataatga aacatcgcaa atcatgaaca atgtcgactc   2220
ggaagcagtg aacacgtcca agatttcaac atattcggct ttcaatttga gcatcaacca   2280
gtctatctct aaacgacgtc gatctcttct gaattctgct cgtgaatctc ctcgtcgtgt   2340
tgcgttggag aattctataa tgtcgatgaa tgggcaaaca atggaagctc tgacagaata   2400
tcgacagaat aaaactatgc agacgagtca agattcgatg ccgagtatga gtttgaacga   2460
ttcgggaaga gatattctcg cgatggtaag aatatctctt tgagtattga atcgaaaatg   2520
tctttcagaa tacatcagtc cgctctcctc atctgaattc ttcaaaaact gctgccccag   2580
gaacaccatc attgatgtca caaaatgtac aacttccacc tccatctcct caattcgaaa   2640
tgccagactt cgatccagct gtggtcaacg ttgtatattt aacatctgaa gatccgtcca   2700
ctgaacaaca tccagaagct ctcaaatttc agcgtattgt tgaaaacgag aaaatgaaag   2760
tacaacacga gattgattct ctgaattcaa ccaatcaact ttctgctgag aaaattgata   2820
tgttgaagac taaggagctc ttgaagttta gtcatgatga gcgagaagcg attatgattg   2880
caagaaaaga cgcggaaatc aagttttttgg agcttcgtct gaaatttgca ctcgagaaaa   2940
aaattgaaag tgaccaggaa attgctgaac tagaacaagg aaattcgaaa atggctgagc   3000
agctaagagg tctcgataag atggctgtcg ttcaaaaaga actagaaaag ctgagaagtc   3060
ttcctccatc acgcgaagag agcgggaaaa tccgaaagga gtggatggag atgaagcaat   3120
gggaattcga ccagaaaatg aaagcactcc gaaatgtacg ctcaaacatg attgcacttc   3180
gttcagagaa aaatgctctc gaaatgaaag tcgcggaaga acacgagaag tttgcccaga   3240
ggaacgattt gaagaaaagt cgaatgctgg tgttctctaa ggctgttaag aaaattgtga   3300
acttctag                                                           3308

<210> SEQ ID NO 5
<211> LENGTH: 3033
<212> TYPE: DNA
<213> ORGANISM: C. elegans

<400> SEQUENCE: 5
atgtcgatgg agcctcgtaa gaagcggaac tcgattctca aggtgcggca agccgtcgaa    60
```

```
accatcgagg aaaccgtcat gaacagtggg cctagttcca caacaactaa tcgacgagtc    120
agctttcata acgtgaagca tgtcaagcag tatgacaggg accatggtaa aattcttgac    180
gccacaccag ttaaggagaa gattactgac actattggat cagatggtat tttgacacca    240
cgtggcggaa acatggatat ttccgaatct ccggcctgca cgtcctcatt tcaagtgttc    300
ggcggtggta atctcgataa aactatggat atgtctctcg aaacaactat caacgagaac    360
aacgaaacgg cgagattgtt tgaaaccaca agagatccaa cactattata cgaaaagatc    420
gtcgaaacca caacaaaagt taccgagcga attgttagta tgccactgga tgatacctta    480
gcaatgttca atacaacgaa tcaagaagat aaggatatgt cagttgatcg ttcagttctt    540
ttcacgattc ccaaagttcc gaagcataac gctacaatga atagaactat accgatggac    600
ctcgatgaat caaaagcagc gggcggccag tgcgatgaaa cgatgaatgt gttcaatttc    660
acaaacttgg aagccgctga aatggatacg agtaaattag atgaaaataa taccatgaat    720
gctatccgga ttccgattaa ttcaaacgtc atgcctgtag acatggacat cactgaacat    780
cacactttaa ttgaagaaaa gaaaaatgat acattcgggc caagtcaact gatggacatt    840
tcggcgccac aagttcaagt taatgatact ttggccattt tcaacagtcc gagagacatc    900
tgtaataagg gtttgggtgt tcctcagaat ctaataaata tcgcctcgaa cgtcgtacct    960
gtggacatgg acatcactga tcaggccgta ttaaacgcgg agaagaaaaa tgatcaattc   1020
gagacaagtc agcttatgga catttctatt ccgaaagttc tagtaaatga cactatggcg   1080
atgttcaaca gcccgaaaca cgtcagtaag agcagcatgg atctcgagaa acgattgaa   1140 gccgctgaca aatcaacgaa atacccgagt atcgcagatg aggtggaaga tttagacatg   1200
gatatggata tcactgaaca acaaccatgt gaggctggta atcagcagaa cgacggcttg   1260
caacttcaaa aggaggattt aatggacatt tcggtgattc gagattcacc tgcagtaaac   1320
gacaccatgg ctgtgttcca gagtcctgcc agagtaaaga tcggagcgaa caactcgatc   1380
attgattcgc agaaatctat cgtgttcggt gacgaaatga gcattgacga gacacaaaat   1440
gatgaaacct tgacgttgcc aaagtcgaat gtagaagtga ctacaactaa tgatgtctac   1500
acgtctctcg agcggcaaga ggaaaatgct tcagaaaacg tatccatgat aaacgaatct   1560
tctgttcatt cggaaatcga caaaaagtcg tttatgctca tcgaagaaga aagggctttt   1620
atgcactcct ccatgattga tgtagcacaa aagttggaag acgatggttc gtcgaagacg   1680
ccagtcatcc ttgcttcaca gtcagcttct cttgccacta agaaccatc agcccttcac   1740 aactcgagtg caactctcaa caattcgatg gaattggaca caatactct tcttaaaact   1800 atgcaaatta caacgtgtga agacattagc atggtccatg agtctattgc tgttgaactg   1860
aacagtaaca aagagcagga gcaattcgga gatgagactt tgcagaaaaa tgatacctcg   1920
aatactggcg cgaatttcac attccaaggc cataatgaaa catcgcaaat catgaacaat   1980
gtcgactcga agcagtgaa cacgtccaag atttcaacat attcggcttt caatttgagc   2040
atcaaccagt ctatctctaa acgacgtcga tctcttctga attctgctcg tgaatctcct   2100
cgtcgtgttg cgttggagaa ttctataatg tcgatgaatg ggcaaacaat ggaagctctg   2160
acagaatatc gacagaataa aactatgcag acgagtcaag attcgatgcc gagtatgagt   2220
ttgaacgatt cggaagagaa tattctcgcg atgaatacat cagtccgctc tcctcatctg   2280
aattcttcaa aaactgctgc cccaggaaca ccatcattga tgtcacaaaa tgtacaactt   2340
ccacctccat ctcctcaatt cgaaatgcca gacttcgatc cagctgtggt caacgttgta   2400
tatttaacat ctgaagatcc gtccactgaa caacatccag aagctctcaa atttcagcgt   2460
```

```
attgttgaaa acgagaaaat gaaagtacaa cacgagattg attctctgaa ttcaaccaat    2520
caactttctg ctgagaaaat tgatatgttg aagactaagg agctcttgaa gtttagtcat    2580
gatgagcgag aagcgattat gattgcaaga aaagacgcgg aaatcaagtt tttggagctt    2640
cgtctgaaat ttgcactcga gaaaaaaatt gaaagtgacc aggaaattgc tgaactagaa    2700
caaggaaatt cgaaaatggc tgagcagcta agaggtctcg ataagatggc tgtcgttcaa    2760
aaagaactag aaaagctgag aagtcttcct ccatcacgcg aagagagcgg gaaaatccga    2820
aaggagtgga tggagatgaa gcaatgggaa ttcgaccaga aaatgaaagc actccgaaat    2880
gtacgctcaa acatgattgc acttcgttca gagaaaaatg ctctcgaaat gaaagtcgcg    2940
gaagaacacg agaagtttgc ccagaggaac gatttgaaga aaagtcgaat gctggtgttc    3000
tctaaggctg ttaagaaaat tgtgaacttc tag                                 3033

<210> SEQ ID NO 6
<211> LENGTH: 7097
<212> TYPE: DNA
<213> ORGANISM: C. elegans

<400> SEQUENCE: 6
accgcatctc ttccaatgga tcaaccatca ttgtcatctt cgccggaaaa tcgtctaaat      60
cccgcacctt ccgttgctga agagcatggc cacagtggac agcacgctga agaagaagaa     120
gacaatgaca cggatgaagt atctgcaatg ccttcttttg tgcctgatga accttcgact     180
cttgttaatt cagatcatga attgtctgat gatgctttaa agtataaaaa tgcagctgcc     240
gaattcaaag cttttgagag aagaatggat tcggtaagaa cagccaaatc agaatgataa     300
ttgaaatttt acatagaata gatttacgta tcaaaaatca aaacctacga atactctcta     360
attcaaaatt taattaatta aaattaaaga tgagatcagc ttcaacaatc acaacatcac     420
tggcaacgcc atcatcttgt gcaccatcaa actcctctga gcctcctact cggtctacac     480
caattatgaa cgatttaggc gttggcccaa ataatcacaa ttggccgtct tcaatgcaag     540
aattatcagg aatttctctg gaaacaccac aggctcgacc gcttggcagc aatagaatta     600
atcagcttgg taggttaata acaaaaaaaa catgattgat tagatttta gttcgaagtg      660 aggctcaaac gggaataagc cttttacaac accatgaaag acctactgtg accgccccat     720
tgagacgaaa tgatatgatg aactcatcac gacagaatcc acagaatgga aatgttcaag     780
atgaaaatcg acccgagcac gtttatgatc aaccaataca tgttcctgga tcatcactgg     840
accgacagaa acttgaaatt gaaattcgac gtcatcgtaa cttgaacata caactgagag     900
acactattgc tcacttggat tatgcagaag aatccgtgca caccacaaaa cgacagctcg     960
aagaaaaaat ttccgaagtc aataatttta agaaagaact gatagaagaa tttaagaaat    1020
gcaaaaaagg agttgaggaa gaatttgaga agaagtttga gaaaattaag gaagattatg    1080
atgaacttta cgagaaattg aagagggatc aacgagatct tgaacgagat cagaagatat    1140
tgaagaaagg aacgggagaa aggaataaag aattcacaga aacggtaatt aagaatttaa    1200
gcaagaaata gttattcgag aaaaaccacg aaatttcgat tgaaaatttt tctcaaagca    1260
aaatctaaaa ttttcattga aataaattga gaatttaaaa agttgaaatt ctattataaa    1320 accttttaatt taaaatccag caaaacttgt caaatttcag atagccactc tccgcgacaa    1380
attaagagca tcagaaacca agaatgcaca atatcgacag gatatacgtg ttcgagacga    1440
aaagctcaag aaaaaagacg aggaaaatcga gaagcttcag aaagacggaa accggctaaa    1500
```

```
gagcactcta cagactttag aaaagcgcgt aaaacaatta cgtactgaaa agaacgcga    1560
cgataaagaa aaggagatgt tcgcgaaggt tgcaatgaat cgaaaaactt cgaatccagt   1620
gccaccagtt ttgaatcaaa gtgttccaat ttcgataaca tcaaatggtc catctagaca   1680
tccatcatca tcttcgttga caacatttag aaaaccatct acatcaaatc gagaaagagg   1740
tgttagttgg gcagatgaac caaatgaaca atcattggaa gctgtaccac aggagttttt   1800
gatggtaata tttagatcaa agcagggttt ttttaaaatt gttttagaa tattgctctg    1860
aaaaaatcaa ttcaaaaaaa atttcaaatt attttttctt cccgactaaa aaattaatat   1920
ttttgaaaaa tagttttta agtctaaaaa tttacagctt actattagca tttgccgaaa    1980
gttccgattt ttcaaaattc ccagaattaa aaatcaatag ttttcgagtt accgaaaatt   2040
gtcaaaaaaa aattttaaat catgcttttt gaagatgcca gtcaaagaaa tgccgggaaa   2100
atttggaaaa tgcacgatct acagagattc tcttggagaa acatctaaag tgacggatac   2160
atgtcaacaa tcaccagcca aaagggata agattattaa ctgagagacg aggggataat    2220
tccctcatac taactctcac tcttcactct ctctgctctt ctcctcattt gtcttctttt   2280
tttgatattg gttgtggttt tttgtcaccg aataataaga atgctatgaa tacatctcac   2340
aattcatttt tctttttctt gcttctcttc cttttttcgt tcttttttgcc gtttgccatg   2400
tgagagtaat aggctgtgaa tgggccagaa ggacactgca caaagtagtc agtcatcaca   2460
ggcttttgtt tatgatgaaa gagagacatt gagaagagga aaagagaag atggaagaaa    2520
aaggcacaag aagtattcaa ctacatgcac cagagaccct tctcttcttt caactatatg   2580
ctttcaatat ccatctcatt tttatgatca tcataacttt tgtgctccac gttcggtttt   2640
aactttgccc agttttaaat tacgttcctc ttgccttcca gttttagaaa ttcagaagct   2700
ctatagatgt aggactctca taagccacaa atatcgtacc tcttcagaaa accttaaaaa   2760
tttccgaaat attgttattt gaagaacaca tgtttcaaga catgaaattt gaaaaacgcc   2820
agaaattccg ttttaccaga aattgaattt atcaattagc tttgaattta tcgatttgtt   2880
actttcaaaa agccaagatt ttgtacacct agattcgaaa ttttgcgatt ttcgacgagg   2940
aaatacggta ctttgcgttt aaaaaaacgt aaaattcttt ggataatagt aattcaaacc   3000
taaaacctaa ataaatttta gatgtttcaa aactttcagt caacttttg gtaaattgcc    3060
aaattctaag aaaatgtggg ctttcccagc aattttgagc ataaatgtaa atctaatttc   3120
tagaaagttg ttagttttt taatccgaaa aaaaactcgt agaaataatt tgttcatttt    3180
taatagagaa tcctccaaaa ttatgataag gactgatatt ttttgacagt gaacaataaa   3240
atttcaatta aaaaaattat atatctatga taatttggca ttttggcgag aatagttct    3300
atcaatttgt ttaactagca aaatacgacc agtttgaaaa tttcattaag acaatccaga   3360
tactcttgaa atagatattc tgggaatagt ttcatttgaa aataaacggt atcctttaaa   3420
cgatcaaggc cgttacttat aacttataaa attatatttt acaaatagtt atctgcaagt   3480
atctacccat tgacatcctt atttaactca tttcttcttt tttcttctta caataataat   3540
aatgtgttca ggatggtcac agtgatacca aaaataataa gttctccata tcctcggaca   3600
cgcctaccac tgtacctcta cactgtttcc atcgtaagaa ttaccaatca atagaaaatt   3660
caagtttaca cctataattc tagattattt cctgctcttt attatactgg aatcttcttt   3720
actgcaaaaa ttatgactgt gtcgttgaga aggaatttcg atggggaagt actcggcact   3780
tactacaggt atcatacaat ttggtaccat aaagaaatga cataactttc agtactttcc   3840
ggtgatagca gctccgatta taatggtaat atcgttttct tggttaataa ttgcaatata   3900
```

```
ttattcaagt agttcatgtg ttcttacatt caattttatg gtaagtttta taggaaggag    3960
gaataaaata aatattgaaa ttaaaggaaa tgccatctgc agtactttgt tctctacttg    4020
gtggtattag ttctgtaata gaaattcatt tttccattga agtaaatcaa gttcaatgga    4080
ctgatcagtg gttactgtca tctgtgggtt taccaatcaa cgattgttta aaaatcgata    4140
ttttcaggga tcttcaatac ttttatgcct tttacatgct acaattgcgt tcacacttca    4200
ataatccttc caacatattt gaatttccaa tcttcttcaa atcgatgtga aaaaacttgt    4260
atcattgttt ttatcaaata tgaaacattt tataggaatc aaaaatatta tgtgaactgt    4320
gatatttact cttgctcaat tcatttcatg taaatattat tttgatactc attactggca    4380
taaattatat tttcgaaatt catgtcacga gcgcggatga tgagggacaa ttcgaattaa    4440
ttctcttttt ctcaacaaaa acaattaaat tttgaacctc cctccgtttt ctttgaaaat    4500
ggcctagaat tgtgatggcc gtggactagc attttcccta gcacgacggc gggaattgtc    4560
tgcgtcatct tcgtcttgca cgctctctcg ttaccccccg ctgtggttat tataccgttt    4620
accaccttaa tcccttcaaa acgcttttat aatttcacat aatctcttct tagaaatctc    4680
aatcgtttat tcagatggga aatcgatcaa agacagacaa tgcaactgcc gtggcatcgc    4740
aaccacccaa aaaagttaaa tcgtaagttt tcttttcctat tttcaaaact aatatatctg    4800
aaatcatcaa catttttagg aaaaagcaaa agaaaatgag cttttcacaa gcacaagacg    4860
tatatcttcg tctgaagcaa gaaaaagaag aggagaaaca acgagagcga gccgaacgag    4920
aaaagcgaaa tgagacgatt gcagcgacaa ataaatcaag aaagaagatg aatcaggcat    4980
tggcaaaaag aaataaaaaa ggacaaccaa atctgaatgc tcaaatggat gtacttctcg    5040
agaggataca gaaaagagtg gataaggaga aaaggagaa gaaatgaact aattgttttg    5100
tctttatat tttcagattt tttttgttga aatgaaattg ttgtgttttt aaaaatcgat    5160
agttttatcg tttcttcgtt tcttaccgat agtatacttt attttctgaa atataattca    5220
attatttatt aaaaacccttt tcagccttca gatggcttcc gatgaaaata tcggtgccga    5280
cggtgaacag aagccttctc ggccgttttt gagaaaagga caaggaacag caagatttag    5340
aatggtagtt tgtgcaaata caaggcttat cgaaataata tatgaagttc agcctagaaa    5400
caacaaaaca tctgctggtg cacctccaac gtcggaactt tcatctgctt caagtccttc    5460
tattaatgtt cctaggttta gtctgtcggt aagtaaaata tcttaaatac aaacgttata    5520
aaactgtggt gactagttaa atataaatat taagtagaat tattccagaa tgctctcccg    5580
aactctgccc gaaccgtgga cagtggaata tcaaatgaag acgagacccg tccaccaacc    5640
aatagctaac ggtcttcttt tcgaatattc caatggagat cttcgatggg ttaatcggca    5700
gaacgctgtt aatgtaagtt ttaattggaa ttttgtcaat taaagtgacc aatttacaga    5760
tctacatatc cgcagttgat aaaacagtca gaattgatct ccccacatac aatatttcaa    5820
ttattcatac atttcaaagg caagttgaag tacttcgtcc tggaaataac ataacattga    5880
taagtattaa acgacgagaa gttcgaactg atttgattta tcaaaacgga atgtataaaa    5940
ctgaaatgta agattatttt cttttttaaa gttcatcgga aatttcgtat ttcagcttca    6000
atagggacgg aagatatgtt acgaaggatt ttagcaatca agaagtttcg agaaagtgag    6060
tctctattca ttttccaatt aattattcag aaaaccatt aaaatctcaa aactattacc    6120
cagatgttta atttaatta atttaattta ttacgataga agatatcgtt aggtagaaaa    6180
aaaaacacac acacattaat agatacaaac catcacaagt ggttacataa ataaattaca    6240
```

| | | | | |
|---|---|---|---|---|
| taaataaaac | gaaacaaaaa | taaaaaaaga | gatgtgacat | tttgcggcaa | aaaatgtctc | 6300 |
| ggcacgataa | aatttagtta | aatgggaaaa | ggcgtgcgcc | tttaaatatt | actgtagttt | 6360 |
| aaaaatcgcg | ttactgtcga | attgttgttt | gccccttttt | tttttgataa | aaacatgttt | 6420 |
| attagtttag | aaaaaagata | aataaaccaa | actacaacag | tctttatagg | cgcacgtatt | 6480 |
| ttcacattta | aaaatctgtc | ctttaacgaa | aaaattgtaa | aatttggcgc | cttcaaagag | 6540 |
| tactgtaatt | tcaaactcaa | tttgaaacag | aattttcatc | gattttcctt | agttagtttt | 6600 |
| tcgatgaatt | ttaatttatt | cattaaaaaa | actcaaataa | gtaaacgat | attttagcaa | 6660 |
| ataatatatt | ttcaaacaaa | acatgtttct | ataattttg | tctaacccaa | aatttaggaa | 6720 |
| tatgacctca | attcttcaaa | aagttagtaa | acaggttta | aaaccccgtt | ataaatattt | 6780 |
| ttgcctctga | aacctatcaa | attttcagat | acaatcccgg | tacacacaca | tatcgcgaca | 6840 |
| atcaatgtcg | ctacgttctc | gtcactgatt | acaacgattt | tgagctcgtt | gagccagaat | 6900 |
| tccgtcttcg | ttggtatcag | ggagatccga | ctggtctcaa | caatcagtat | attctcaaga | 6960 |
| tcattggacg | acctgaatgc | agcgagaaaa | cattgagact | tgaagtgaat | cttccacgt | 7020 |
| gtgaaggtac | attggaaact | gcagagatga | taggcgataa | acgtcggaaa | acaactttgt | 7080 |
| tccagtggaa | aaaatga | | | | | 7097 |

```
<210> SEQ ID NO 7
<211> LENGTH: 3624
<212> TYPE: DNA
<213> ORGANISM: C. elegans

<400> SEQUENCE: 7
```

| | | | | | | |
|---|---|---|---|---|---|---|
| atgtcaacaa | tcaccagcca | aaagggata | agattattaa | ctgagagacg | aggggataat | 60 |
| tccctcatac | taactctcac | tcttcactct | ctctgctctt | ctcctcattt | gtcttctttt | 120 |
| tttgatattg | gttgtggttt | tttgtcaccg | aataataaga | atgctatgaa | tacatctcac | 180 |
| aattcatttt | tcttttttctt | gcttctcttc | cttttttcgt | tcttttttgcc | gtttgccatt | 240 |
| caactttttg | gtaaattgcc | aaattctaag | aaaatgtggg | ctttcccagc | aattttgagc | 300 |
| ataaatgtaa | atctaatttc | tagaaagttg | atggtcacag | tgataccaaa | aataataagt | 360 |
| tctccatatc | ctcggacacg | cctaccactg | tacctctaca | ctgtttccat | cattatttcc | 420 |
| tgctctttat | tatactggaa | tcttctttac | tgcaaaaatt | atgactgtgt | cgttgagaag | 480 |
| gaatttcgat | ggggaagtac | tcggcactta | ctacagtact | ttccggtgat | agcagctccg | 540 |
| attataatgg | taatatcgtt | tcttggtta | ataattgcaa | tatattattc | aagtagttca | 600 |
| tgtgttctta | cattcaattt | tatgaaatg | ccatctgcag | tactttgttc | tctacttggt | 660 |
| ggtattagtt | ctgtaataga | aattcatttt | tccattgaag | taaatcaagt | tcaatggact | 720 |
| gatcagtggt | tactgtcatc | tgtgggttta | ccaatcaacg | attgtttaaa | aatcgatatt | 780 |
| ttcagggatc | ttcaatactt | ttatgccttt | tacatgctac | aattgcgttc | acacttcaat | 840 |
| aatccttcca | acatatttga | atttccaatc | ttcttcaaat | cgatgaatca | aaaatattat | 900 |
| gtgaactgtg | atatttactc | ttgctcaatt | catttcatga | aaagcaaaa | gaaaatgagc | 960 |
| ttttcacaag | cacaagacgt | atatcttcgt | ctgaagcaag | aaaaagaaga | ggagaaacaa | 1020 |
| cgagagcgag | ccgaacgaga | aaagcgaaat | gagacgattg | cagcgacaaa | taatcaaga | 1080 |
| aagaagatga | atcaggcatt | ggcaaaaaga | aataaaaaag | gacaaccaaa | tctgaatgct | 1140 |
| caaatggata | tggcttccga | tgaaaatatc | ggtgccgacg | tgaacagaa | gccttctcgg | 1200 |
| ccgttttga | gaaaaggaca | aggaacagca | agatttagaa | tggtagtttg | tgcaaataca | 1260 |

```
aggcttatcg aaataatata tgaagttcag cctagaaaca acaaaacatc tgctggtgca   1320
cctccaacgt cggaactttc atctgcttca agtccttcta ttaatgttcc taggtttagt   1380
ctgtcgaatg ctctcccgaa ctctgcccga accgtggaca gtggaatatc aaatgaagac   1440
gagacccgtc caccaaccac cgcatctctt ccaatggatc aaccatcatt gtcatcttcg   1500
ccggaaaatc gtctaaatcc cgcaccttcc gttgctgaag agcatggcca cagtggacag   1560
cacgctgaag aagaagaaga caatgacacg gatgaagtat ctgcaatgcc ttcttttgtg   1620
cctgatgaac cttcgactct tgttaattca gatcatgaat tgtctgatga tgctttaaag   1680
tataaaaatg cagctgccga attcaaagct tttgagagaa gaatggattc gatgagatca   1740
gcttcaacaa tcacaacatc actggcaacg ccatcatctt gtgcaccatc aaactcctct   1800
gagcctccta ctcggtctac accaattatg aacgatttag gcgttggccc aaataatcac   1860
aattggccgt cttcaatgca agaattatca ggaatttctc tggaaacacc acaggctcga   1920
ccgcttggca gcaatagaat taatcagctt gttcgaagtg aggctcaaac gggaataagc   1980
cttttacaac accatgaaag acctactgtg accgccccat tgagacgaaa tgatatgatg   2040
aactcatcac gacagaatcc acagaatgga atgttcaag atgaaaatcg acccgagcac   2100
gtttatgatc aaccaataca tgttcctgga tcatcactgg accgacagaa acttgaaatt   2160
gaaattcgac gtcatcgtaa cttgaacata caactgagag cactattgc tcacttggat   2220 tatgcagaag aatccgtgca caccacaaaa cgacagctcg aagaaaaaat ttccgaagtc   2280
aataatttta agaaagaact gatagaagaa tttaagaaat gcaaaaagg agttgaggaa   2340 gaatttgaga gaagtttga gaaaattaag gaagattatg atgaacttta cgagaaattg   2400
aagagggatc aacgagatct tgaacgagat cagaagatat tgaagaaagg aacgggagaa   2460
aggaataaag aattcacaga aacgatagcc actctccgcg acaaattaag agcatcagaa   2520
accaagaatg cacaatatcg acaggatata cgtgttcgag acgaaaagct caagaaaaaa   2580
gacgaggaaa tcgagaagct tcagaaagac ggaaaccggc taaagagcac tctacagact   2640
ttagaaaagc gcgtaaaaca attacgtact gaaaagaac gcgacgataa agaaaaggag   2700
atgttcgcga aggttgcaat gaatcgaaaa acttcgaatc cagtgccacc agttttgaat   2760
caaagtgttc caatttcgat aacatcaaat ggtccatcta gacatccatc atcatcttcg   2820
ttgacaacat ttagaaaacc atctacatca aatcgagaaa gaggtgttag ttgggcagat   2880
gaaccaaatg aacaatcatt ggaagctgta ccacaggagt ttttgatgat gccagtcaaa   2940
gaaatgccgg aaaatttgg aaaatgcacg atctacagag attctcttgg agaaacatct   3000
aaagtgacgg atacaatagc taacggtctt cttttcgaat attccaatgg agatcttcga   3060
tgggttaatc ggcagaacgc tgttaatatc tacatatccg cagttgataa aacagtcaga   3120
attgatctcc ccacatacaa tatttcaatt attcatacat ttcaaaggca agttgaagta   3180
cttcgtcctg gaaataacat aacattgata agtattaaac gacgagaagt tcgaactgat   3240
ttgatttatc aaaacggaat gtataaaact gaaatcttca ataggacgg aagatatgtt   3300 acgaaggatt ttagcaatca agaagtttcg agaaaataca atcccggtac acacacatat   3360
cgcgacaatc aatgtcgcta cgttctcgtc actgattaca acgattttga gctcgttgag   3420
ccagaattcc gtcttcgttg gtatcaggga gatccgactg gtctcaacaa tcagtatatt   3480
ctcaagatca ttggacgacc tgaatgcagc gagaaaacat tgagacttga agtgaatctt   3540
tccacgtgtg aaggtacatt ggaaactgca gagatgatag gcgataaacg tcggaaaaca   3600
```
actttgttcc agtggaaaaa atga                                          3624

<210> SEQ ID NO 8
<211> LENGTH: 336
<212> TYPE: PRT
<213> ORGANISM: C. elegans

<400> SEQUENCE: 8

Met Asn Arg Leu Lys Ser Asp Gln Lys Thr Lys Leu Arg Gln Phe Val
1               5                   10                  15

Gln Trp Thr Gln Val Thr Glu Ala Val Ser Leu Asn Phe Leu Ala Lys
            20                  25                  30

Ala Asn Trp Asn Ile Glu Tyr Ala Met Thr Leu Tyr Phe Asp Asn Pro
        35                  40                  45

Asn Leu Phe Ala Gly Ser Thr Pro Gln Pro Ser Val Asp Arg Ser Asn
    50                  55                  60

Ile Glu Arg Leu Phe Asn Gln Tyr Val Asp Pro Lys Asp Lys Val Gly
65                  70                  75                  80

Glu Lys Arg Met Gly Pro His Gly Ile Asn Arg Leu Leu Thr Asp Leu
                85                  90                  95

Gly Tyr Glu Ala Thr Asp Arg Arg Val Leu Val Leu Ala Trp Lys Phe
            100                 105                 110

Thr Ala Gln Thr Gln Cys Glu Phe Ser Leu Asp Glu Trp Val Lys Gly
        115                 120                 125

Met Thr Ala Leu Gln Ala Asp Thr Val Gln Asn Leu Arg Gln Arg Ile
    130                 135                 140

Asp Ser Ile Asn Ser Gly Leu Glu Ser Asp Lys Ala Lys Phe His Glu
145                 150                 155                 160

Leu Tyr Leu Phe Ala Phe Asn Tyr Ala Lys Ser Ala Ala Cys Arg Asn
                165                 170                 175

Leu Asp Leu Glu Thr Ala Ile Cys Cys Trp Asp Val Leu Phe Gly Gln
            180                 185                 190

Arg Ser Thr Ile Met Thr Gln Trp Ile Asp Phe Leu Trp Ala Gln Glu
        195                 200                 205

Asn Ala Ala Ala Ser Arg Leu Ala Gln Asn Val Gly Ala Ser Asn Ala
    210                 215                 220

Lys Gln Phe Lys Ser Val Trp Ile Ser Arg Asp Thr Trp Asn Leu Phe
225                 230                 235                 240

Trp Asp Phe Ile Leu Leu Ser Lys Pro Asp Leu Ser Asp Tyr Asp Asp
                245                 250                 255

Glu Gly Ala Trp Pro Val Leu Ile Asp Gln Phe Val Asp Tyr Cys Arg
            260                 265                 270

Glu Asn Leu Asn Tyr Pro Lys Pro Gly Asn Ala Ser Asn Asp Gln Gln
        275                 280                 285

Met Glu Thr Pro Lys Ile Ala Gln Lys Pro Gly Ile Phe Tyr Phe
    290                 295                 300

Asn Ser Asn Leu Gln Leu Ile Glu Phe Lys Leu Phe Gln Tyr Pro Met
305                 310                 315                 320

Leu Lys Thr Ile Phe Lys Ile Thr Ile His Thr Ala Gly Thr Asn Arg
                325                 330                 335

<210> SEQ ID NO 9
<211> LENGTH: 283
<212> TYPE: PRT
<213> ORGANISM: C. elegans

<400> SEQUENCE: 9

```
Met Asn Arg Leu Lys Ser Asp Gln Lys Thr Lys Ile Glu Arg Leu Phe
1               5                   10                  15

Asn Gln Tyr Val Asp Pro Lys Asp Lys Val Gly Glu Lys Arg Met Gly
            20                  25                  30

Pro His Gly Ile Asn Arg Leu Leu Thr Asp Leu Gly Tyr Glu Ala Thr
        35                  40                  45

Asp Arg Arg Val Leu Val Leu Ala Trp Lys Phe Thr Ala Gln Thr Gln
    50                  55                  60

Cys Glu Phe Ser Leu Asp Glu Trp Val Lys Gly Met Thr Ala Leu Gln
65                  70                  75                  80

Ala Asp Thr Val Gln Asn Leu Arg Gln Arg Ile Asp Ser Ile Asn Ser
                85                  90                  95

Gly Leu Glu Ser Asp Lys Ala Lys Phe His Glu Leu Tyr Leu Phe Ala
            100                 105                 110

Phe Asn Tyr Ala Lys Ser Ala Ala Cys Arg Asn Leu Asp Leu Glu Thr
        115                 120                 125

Ala Ile Cys Cys Trp Asp Val Leu Phe Gly Gln Arg Ser Thr Ile Met
    130                 135                 140

Thr Gln Trp Ile Asp Phe Leu Trp Ala Gln Glu Asn Ala Ala Ala Ser
145                 150                 155                 160

Arg Leu Ala Gln Asn Val Gly Ala Ser Asn Ala Lys Gln Phe Lys Ser
                165                 170                 175

Val Trp Ile Ser Arg Asp Thr Trp Asn Leu Phe Trp Asp Phe Ile Leu
            180                 185                 190

Leu Ser Lys Pro Asp Leu Ser Asp Tyr Asp Asp Glu Gly Ala Trp Pro
        195                 200                 205

Val Leu Ile Asp Gln Phe Val Asp Tyr Cys Arg Glu Asn Leu Asn Tyr
    210                 215                 220

Pro Lys Pro Gly Asn Ala Ser Asn Asp Gln Met Glu Thr Pro Lys
225                 230                 235                 240

Ile Ala Gln Lys Lys Pro Gly Ile Phe Tyr Phe Asn Ser Asn Leu Gln
                245                 250                 255

Leu Ile Glu Phe Lys Leu Phe Gln Tyr Pro Met Leu Lys Thr Ile Phe
            260                 265                 270

Lys Ile Thr Ile His Thr Ala Gly Thr Asn Arg
        275                 280
```

<210> SEQ ID NO 10
<211> LENGTH: 1010
<212> TYPE: PRT
<213> ORGANISM: C. elegans

<400> SEQUENCE: 10

```
Met Ser Met Glu Pro Arg Lys Lys Arg Asn Ser Ile Leu Lys Val Arg
1               5                   10                  15

Gln Ala Val Glu Thr Ile Glu Glu Thr Val Met Asn Ser Gly Pro Ser
            20                  25                  30

Ser Thr Thr Thr Asn Arg Arg Val Ser Phe His Asn Val Lys His Val
        35                  40                  45

Lys Gln Tyr Asp Arg Asp His Gly Lys Ile Leu Asp Ala Thr Pro Val
    50                  55                  60

Lys Glu Lys Ile Thr Asp Thr Ile Gly Ser Asp Gly Ile Leu Thr Pro
65                  70                  75                  80
```

-continued

Arg Gly Gly Asn Met Asp Ile Ser Glu Ser Pro Ala Cys Thr Ser Ser
                85                  90                  95

Phe Gln Val Phe Gly Gly Asn Leu Asp Lys Thr Met Asp Met Ser
            100                 105                 110

Leu Glu Thr Thr Ile Asn Glu Asn Asn Glu Thr Ala Arg Leu Phe Glu
            115                 120                 125

Thr Thr Arg Asp Pro Thr Leu Leu Tyr Glu Lys Ile Val Glu Thr Thr
        130                 135                 140

Thr Lys Val Thr Glu Arg Ile Val Ser Met Pro Leu Asp Asp Thr Leu
145                 150                 155                 160

Ala Met Phe Asn Thr Thr Asn Gln Glu Asp Lys Asp Met Ser Val Asp
                165                 170                 175

Arg Ser Val Leu Phe Thr Ile Pro Lys Val Pro Lys His Asn Ala Thr
            180                 185                 190

Met Asn Arg Thr Ile Pro Met Asp Leu Asp Glu Ser Lys Ala Ala Gly
        195                 200                 205

Gly Gln Cys Asp Glu Thr Met Asn Val Phe Asn Phe Thr Asn Leu Glu
    210                 215                 220

Ala Ala Glu Met Asp Thr Ser Lys Leu Asp Glu Asn Asn Thr Met Asn
225                 230                 235                 240

Ala Ile Arg Ile Pro Ile Asn Ser Asn Val Met Pro Val Asp Met Asp
                245                 250                 255

Ile Thr Glu His His Thr Leu Ile Glu Glu Lys Lys Asn Asp Thr Phe
            260                 265                 270

Gly Pro Ser Gln Leu Met Asp Ile Ser Ala Pro Gln Val Gln Val Asn
        275                 280                 285

Asp Thr Leu Ala Ile Phe Asn Ser Pro Arg Asp Ile Cys Asn Lys Gly
    290                 295                 300

Leu Gly Val Pro Gln Asn Leu Ile Asn Ile Ala Ser Asn Val Val Pro
305                 310                 315                 320

Val Asp Met Asp Ile Thr Asp Gln Ala Val Leu Asn Ala Glu Lys Lys
                325                 330                 335

Asn Asp Gln Phe Glu Thr Ser Gln Leu Met Asp Ile Ser Ile Pro Lys
            340                 345                 350

Val Leu Val Asn Asp Thr Met Ala Met Phe Asn Ser Pro Lys His Val
        355                 360                 365

Ser Lys Ser Ser Met Asp Leu Glu Lys Thr Ile Glu Ala Ala Asp Lys
    370                 375                 380

Ser Thr Lys Tyr Pro Ser Ile Ala Asp Glu Val Glu Asp Leu Asp Met
385                 390                 395                 400

Asp Met Asp Ile Thr Glu Gln Gln Pro Cys Glu Ala Gly Asn Gln Gln
                405                 410                 415

Asn Asp Gly Leu Gln Leu Gln Lys Glu Asp Leu Met Asp Ile Ser Val
            420                 425                 430

Ile Arg Asp Ser Pro Ala Val Asn Asp Thr Met Ala Val Phe Gln Ser
        435                 440                 445

Pro Ala Arg Val Lys Ile Gly Ala Asn Asn Ser Ile Ile Asp Ser Gln
    450                 455                 460

Lys Ser Ile Val Phe Gly Asp Glu Met Ser Ile Asp Glu Thr Gln Asn
465                 470                 475                 480

Asp Gly Thr Leu Thr Leu Pro Lys Ser Asn Val Glu Val Thr Thr
                485                 490                 495

Asn Asp Val Tyr Thr Ser Leu Glu Arg Gln Glu Glu Asn Ala Ser Glu

-continued

```
                500                 505                 510
Asn Val Ser Met Ile Asn Glu Ser Ser Val His Ser Glu Ile Asp Lys
        515                 520                 525
Lys Ser Phe Met Leu Ile Glu Glu Arg Ala Phe Met His Ser Ser
        530                 535                 540
Met Ile Asp Val Ala Gln Lys Leu Glu Asp Asp Gly Ser Ser Lys Thr
545                 550                 555                 560
Pro Val Ile Leu Ala Ser Gln Ser Ala Ser Leu Ala Thr Lys Glu Pro
                565                 570                 575
Ser Ala Leu His Asn Ser Ser Ala Thr Leu Asn Asn Ser Met Glu Leu
                580                 585                 590
Asp Asn Asn Thr Leu Leu Lys Thr Met Gln Ile Thr Thr Cys Glu Asp
                595                 600                 605
Ile Ser Met Val His Glu Ser Ile Ala Val Glu Leu Asn Ser Asn Lys
                610                 615                 620
Glu Gln Glu Gln Phe Gly Asp Glu Thr Leu Gln Lys Asn Asp Thr Ser
625                 630                 635                 640
Asn Thr Gly Ala Asn Phe Thr Phe Gln Gly His Asn Glu Thr Ser Gln
                645                 650                 655
Ile Met Asn Asn Val Asp Ser Glu Ala Val Asn Thr Ser Lys Ile Ser
                660                 665                 670
Thr Tyr Ser Ala Phe Asn Leu Ser Ile Asn Gln Ser Ile Ser Lys Arg
                675                 680                 685
Arg Arg Ser Leu Leu Asn Ser Ala Arg Glu Ser Pro Arg Arg Val Ala
                690                 695                 700
Leu Glu Asn Ser Ile Met Ser Met Asn Gly Gln Thr Met Glu Ala Leu
705                 710                 715                 720
Thr Glu Tyr Arg Gln Asn Lys Thr Met Gln Thr Ser Gln Asp Ser Met
                725                 730                 735
Pro Ser Met Ser Leu Asn Asp Ser Gly Arg Asp Ile Leu Ala Met Asn
                740                 745                 750
Thr Ser Val Arg Ser Pro His Leu Asn Ser Ser Lys Thr Ala Ala Pro
                755                 760                 765
Gly Thr Pro Ser Leu Met Ser Gln Asn Val Gln Leu Pro Pro Pro Ser
770                 775                 780
Pro Gln Phe Glu Met Pro Asp Phe Asp Pro Ala Val Val Asn Val Val
785                 790                 795                 800
Tyr Leu Thr Ser Glu Asp Pro Ser Thr Glu Gln His Pro Glu Ala Leu
                805                 810                 815
Lys Phe Gln Arg Ile Val Glu Asn Glu Lys Met Lys Val Gln His Glu
                820                 825                 830
Ile Asp Ser Leu Asn Ser Thr Asn Gln Leu Ser Ala Glu Lys Ile Asp
                835                 840                 845
Met Leu Lys Thr Lys Glu Leu Leu Lys Phe Ser His Asp Glu Arg Glu
                850                 855                 860
Ala Ile Met Ile Ala Arg Lys Asp Ala Glu Ile Lys Phe Leu Glu Leu
865                 870                 875                 880
Arg Leu Lys Phe Ala Leu Glu Lys Lys Ile Glu Ser Asp Gln Glu Ile
                885                 890                 895
Ala Glu Leu Glu Gln Gly Asn Ser Lys Met Ala Glu Gln Leu Arg Gly
                900                 905                 910
Leu Asp Lys Met Ala Val Val Gln Lys Glu Leu Glu Lys Leu Arg Ser
                915                 920                 925
```

```
Leu Pro Pro Ser Arg Glu Glu Ser Gly Lys Ile Arg Lys Glu Trp Met
        930                 935                 940

Glu Met Lys Gln Trp Glu Phe Asp Gln Lys Met Lys Ala Leu Arg Asn
945                 950                 955                 960

Val Arg Ser Asn Met Ile Ala Leu Arg Ser Glu Lys Asn Ala Leu Glu
                965                 970                 975

Met Lys Val Ala Glu His Glu Lys Phe Ala Gln Arg Asn Asp Leu
            980                 985                 990

Lys Lys Ser Arg Met Leu Val Phe  Ser Lys Ala Val Lys  Lys Ile Val
        995                 1000                1005

Asn Phe
    1010

<210> SEQ ID NO 11
<211> LENGTH: 1207
<212> TYPE: PRT
<213> ORGANISM: C. elegans

<400> SEQUENCE: 11

Met Ser Thr Ile Thr Ser Gln Lys Gly Ile Arg Leu Leu Thr Glu Arg
1               5                   10                  15

Arg Gly Asp Asn Ser Leu Ile Leu Thr Leu Thr Leu His Ser Leu Cys
            20                  25                  30

Ser Ser Pro His Leu Ser Ser Phe Phe Asp Ile Gly Cys Gly Phe Leu
        35                  40                  45

Ser Pro Asn Asn Lys Asn Ala Met Asn Thr Ser His Asn Ser Phe Phe
    50                  55                  60

Phe Phe Leu Leu Leu Phe Leu Phe Ser Phe Leu Pro Phe Ala Ile
65                  70                  75                  80

Gln Leu Phe Gly Lys Leu Pro Asn Ser Lys Met Trp Ala Phe Pro
                85                  90                  95

Ala Ile Leu Ser Ile Asn Val Asn Leu Ile Ser Arg Lys Leu Met Val
            100                 105                 110

Thr Val Ile Pro Lys Ile Ile Ser Ser Pro Tyr Pro Arg Thr Arg Leu
        115                 120                 125

Pro Leu Tyr Leu Tyr Thr Val Ser Ile Ile Ser Cys Ser Leu Leu
    130                 135                 140

Tyr Trp Asn Leu Leu Tyr Cys Lys Asn Tyr Asp Cys Val Val Glu Lys
145                 150                 155                 160

Glu Phe Arg Trp Gly Ser Thr Arg His Leu Leu Gln Tyr Phe Pro Val
                165                 170                 175

Ile Ala Ala Pro Ile Ile Met Val Ile Ser Phe Ser Trp Leu Ile Ile
            180                 185                 190

Ala Ile Tyr Tyr Ser Ser Ser Cys Val Leu Thr Phe Asn Phe Met
        195                 200                 205

Glu Met Pro Ser Ala Val Leu Cys Ser Leu Leu Gly Gly Ile Ser Ser
    210                 215                 220

Val Ile Glu Ile His Phe Ser Ile Glu Val Asn Val Gln Trp Thr
225                 230                 235                 240

Asp Gln Trp Leu Leu Ser Ser Val Gly Leu Pro Ile Asn Asp Cys Leu
                245                 250                 255

Lys Ile Asp Ile Phe Arg Asp Leu Gln Tyr Phe Tyr Ala Phe Tyr Met
            260                 265                 270

Leu Gln Leu Arg Ser His Phe Asn Asn Pro Ser Asn Ile Phe Glu Phe
```

-continued

```
                275                 280                 285
Pro Ile Phe Phe Lys Ser Met Asn Gln Lys Tyr Tyr Val Asn Cys Asp
290                 295                 300
Ile Tyr Ser Cys Ser Ile His Phe Met Lys Lys Gln Lys Lys Met Ser
305                 310                 315                 320
Phe Ser Gln Ala Gln Asp Val Tyr Leu Arg Leu Lys Gln Glu Lys Glu
                325                 330                 335
Glu Lys Gln Arg Glu Arg Ala Glu Arg Lys Arg Asn Glu Thr
                340                 345                 350
Ile Ala Ala Thr Asn Lys Ser Arg Lys Lys Met Asn Gln Ala Leu Ala
                355                 360                 365
Lys Arg Asn Lys Lys Gly Gln Pro Asn Leu Asn Ala Gln Met Asp Met
370                 375                 380
Ala Ser Asp Glu Asn Ile Gly Ala Asp Gly Glu Gln Lys Pro Ser Arg
385                 390                 395                 400
Pro Phe Leu Arg Lys Gly Gln Gly Thr Ala Arg Phe Arg Met Val Val
                405                 410                 415
Cys Ala Asn Thr Arg Leu Ile Glu Ile Ile Tyr Glu Val Gln Pro Arg
                420                 425                 430
Asn Asn Lys Thr Ser Ala Gly Ala Pro Pro Thr Ser Glu Leu Ser Ser
                435                 440                 445
Ala Ser Ser Pro Ser Ile Asn Val Pro Arg Phe Ser Leu Ser Asn Ala
450                 455                 460
Leu Pro Asn Ser Ala Arg Thr Val Asp Ser Gly Ile Ser Asn Glu Asp
465                 470                 475                 480
Glu Thr Arg Pro Pro Thr Thr Ala Ser Leu Pro Met Asp Gln Pro Ser
                485                 490                 495
Leu Ser Ser Ser Pro Glu Asn Arg Leu Asn Pro Ala Pro Ser Val Ala
                500                 505                 510
Glu Glu His Gly His Ser Gly Gln His Ala Glu Glu Glu Asp Asn
                515                 520                 525
Asp Thr Asp Glu Val Ser Ala Met Pro Ser Phe Val Pro Asp Glu Pro
530                 535                 540
Ser Thr Leu Val Asn Ser Asp His Glu Leu Ser Asp Asp Ala Leu Lys
545                 550                 555                 560
Tyr Lys Asn Ala Ala Ala Glu Phe Lys Ala Phe Glu Arg Arg Met Asp
                565                 570                 575
Ser Met Arg Ser Ala Ser Thr Ile Thr Thr Ser Leu Ala Thr Pro Ser
                580                 585                 590
Ser Cys Ala Pro Ser Asn Ser Ser Glu Pro Pro Thr Arg Ser Thr Pro
                595                 600                 605
Ile Met Asn Asp Leu Gly Val Gly Pro Asn Asn His Asn Trp Pro Ser
610                 615                 620
Ser Met Gln Glu Leu Ser Gly Ile Ser Leu Glu Thr Pro Gln Ala Arg
625                 630                 635                 640
Pro Leu Gly Ser Asn Arg Ile Asn Gln Leu Val Arg Ser Glu Ala Gln
                645                 650                 655
Thr Gly Ile Ser Leu Leu Gln His His Glu Arg Pro Thr Val Thr Ala
                660                 665                 670
Pro Leu Arg Arg Asn Asp Met Met Asn Ser Ser Arg Gln Asn Pro Gln
                675                 680                 685
Asn Gly Asn Val Gln Asp Glu Asn Arg Pro Glu His Val Tyr Asp Gln
                690                 695                 700
```

-continued

```
Pro Ile His Val Pro Gly Ser Ser Leu Asp Arg Gln Lys Leu Glu Ile
705                 710                 715                 720

Glu Ile Arg Arg His Arg Asn Leu Asn Ile Gln Leu Arg Asp Thr Ile
                    725                 730                 735

Ala His Leu Asp Tyr Ala Glu Glu Ser Val His Thr Thr Lys Arg Gln
                740                 745                 750

Leu Glu Glu Lys Ile Ser Glu Val Asn Asn Phe Lys Lys Glu Leu Ile
            755                 760                 765

Glu Glu Phe Lys Lys Cys Lys Lys Gly Val Glu Glu Phe Glu Lys
770                 775                 780

Lys Phe Glu Lys Ile Lys Glu Asp Tyr Asp Glu Leu Tyr Glu Lys Leu
785                 790                 795                 800

Lys Arg Asp Gln Arg Asp Leu Glu Arg Asp Gln Lys Ile Leu Lys Lys
                805                 810                 815

Gly Thr Gly Glu Arg Asn Lys Glu Phe Thr Glu Thr Ile Ala Thr Leu
                820                 825                 830

Arg Asp Lys Leu Arg Ala Ser Glu Thr Lys Asn Ala Gln Tyr Arg Gln
                835                 840                 845

Asp Ile Arg Val Arg Asp Glu Lys Leu Lys Lys Lys Asp Glu Glu Ile
                850                 855                 860

Glu Lys Leu Gln Lys Asp Gly Asn Arg Leu Lys Ser Thr Leu Gln Thr
865                 870                 875                 880

Leu Glu Lys Arg Val Lys Gln Leu Arg Thr Glu Lys Glu Arg Asp Asp
                885                 890                 895

Lys Glu Lys Glu Met Phe Ala Lys Val Ala Met Asn Arg Lys Thr Ser
                900                 905                 910

Asn Pro Val Pro Pro Val Leu Asn Gln Ser Val Pro Ile Ser Ile Thr
                915                 920                 925

Ser Asn Gly Pro Ser Arg His Pro Ser Ser Ser Leu Thr Thr Phe
                930                 935                 940

Arg Lys Pro Ser Thr Ser Asn Arg Glu Arg Gly Val Ser Trp Ala Asp
945                 950                 955                 960

Glu Pro Asn Glu Gln Ser Leu Glu Ala Val Pro Gln Glu Phe Leu Met
                965                 970                 975

Met Pro Val Lys Glu Met Pro Gly Lys Phe Gly Lys Cys Thr Ile Tyr
                980                 985                 990

Arg Asp Ser Leu Gly Glu Thr Ser  Lys Val Thr Asp Thr  Ile Ala Asn
                995                 1000                1005

Gly Leu  Leu Phe Glu Tyr  Ser Asn Gly Asp Leu Arg  Trp Val Asn
    1010                 1015                1020

Arg Gln  Asn Ala Val Asn Ile  Tyr Ile Ser Ala Val  Asp Lys Thr
    1025                 1030                1035

Val Arg  Ile Asp Leu Pro Thr  Tyr Asn Ile Ser Ile  Ile His Thr
    1040                 1045                1050

Phe Gln  Arg Gln Val Glu Val  Leu Arg Pro Gly Asn  Asn Ile Thr
    1055                 1060                1065

Leu Ile  Ser Ile Lys Arg Arg  Glu Val Arg Thr Asp  Leu Ile Tyr
    1070                 1075                1080

Gln Asn  Gly Met Tyr Lys Thr  Glu Ile Phe Asn Arg  Asp Gly Arg
    1085                 1090                1095

Tyr Val  Thr Lys Asp Phe Ser  Asn Gln Glu Val Ser  Arg Lys Tyr
    1100                 1105                1110
```

```
Asn Pro Gly Thr His Thr Tyr Arg Asp Asn Gln Cys Arg Tyr Val
    1115                1120                1125

Leu Val Thr Asp Tyr Asn Asp Phe Glu Leu Val Glu Pro Glu Phe
    1130                1135                1140

Arg Leu Arg Trp Tyr Gln Gly Asp Pro Thr Gly Leu Asn Asn Gln
    1145                1150                1155

Tyr Ile Leu Lys Ile Ile Gly Arg Pro Glu Cys Ser Glu Lys Thr
    1160                1165                1170

Leu Arg Leu Glu Val Asn Leu Ser Thr Cys Glu Gly Thr Leu Glu
    1175                1180                1185

Thr Ala Glu Met Ile Gly Asp Lys Arg Lys Thr Thr Leu Phe
    1190                1195                1200

Gln Trp Lys Lys
    1205

<210> SEQ ID NO 12
<211> LENGTH: 780
<212> TYPE: DNA
<213> ORGANISM: homo sapiens

<400> SEQUENCE: 12
atgaacaagt tgaaatcatc gcagaaggat aaagttcgtc agtttatgat cttcacacaa    60
tctagtgaaa aaacagcagt aagttgtctt tctcaaaatg actggaagtt agatgttgca   120
acagataatt ttttccaaaa tcctgaactt tatatacgag agagtgtaaa aggatcattg   180
gacaggaaga agttagaaca gctgtacaat agatacaaag accctcaaga tgagaataaa   240
attggaatag atggcataca gcagttctgt gatgacctgg cactcgatcc agccagcatt   300
agtgtgttga ttattgcgtg gaagttcaga gcagcaacac agtgcgagtt ctccaaacag   360
gagttcatgg atggcatgac agaattagga tgtgacagca tagaacaact aaaggcccag   420
atacccaaga tggaacaaga attgaaagaa ccaggacgat taaggatttt taccagtttt   480
acttttaatt ttgcaaagaa tccaggacaa aaaggattag atctagaaat ggccattgcc   540
tactggaact tagtgcttaa tggaagattt aaattcttag acttatggaa taaattttttg   600 ttggaacatc ataaacgatc aataccaaaa gacacttgga atcttctttt agacttcagt   660
acgatgattg cagatgacat gtctaattat gatgaagaag gagcatggcc tgttcttatt   720
gatgactttg tggaatttgc acgccctcaa attgctggga caaaaagtac aacagtgtag   780

<210> SEQ ID NO 13
<211> LENGTH: 259
<212> TYPE: PRT
<213> ORGANISM: homo sapiens

<400> SEQUENCE: 13

Met Asn Lys Leu Lys Ser Ser Gln Lys Asp Lys Val Arg Gln Phe Met
1               5                   10                  15

Ile Phe Thr Gln Ser Ser Glu Lys Thr Ala Val Ser Cys Leu Ser Gln
            20                  25                  30

Asn Asp Trp Lys Leu Asp Val Ala Thr Asp Asn Phe Phe Gln Asn Pro
        35                  40                  45

Glu Leu Tyr Ile Arg Glu Ser Val Lys Gly Ser Leu Asp Arg Lys Lys
    50                  55                  60

Leu Glu Gln Leu Tyr Asn Arg Tyr Lys Asp Pro Gln Asp Glu Asn Lys
65                  70                  75                  80

Ile Gly Ile Asp Gly Ile Gln Gln Phe Cys Asp Asp Leu Ala Leu Asp
```

```
                85                  90                  95
Pro Ala Ser Ile Ser Val Leu Ile Ile Ala Trp Lys Phe Arg Ala Ala
            100                 105                 110
Thr Gln Cys Glu Phe Ser Lys Gln Glu Phe Met Asp Gly Met Thr Glu
        115                 120                 125
Leu Gly Cys Asp Ser Ile Glu Gln Leu Lys Ala Gln Ile Pro Lys Met
    130                 135                 140
Glu Gln Glu Leu Lys Glu Pro Gly Arg Phe Lys Asp Phe Tyr Gln Phe
145                 150                 155                 160
Thr Phe Asn Phe Ala Lys Asn Pro Gly Gln Lys Gly Leu Asp Leu Glu
                165                 170                 175
Met Ala Ile Ala Tyr Trp Asn Leu Val Leu Asn Gly Arg Phe Lys Phe
            180                 185                 190
Leu Asp Leu Trp Asn Lys Phe Leu Leu Glu His His Lys Arg Ser Ile
        195                 200                 205
Pro Lys Asp Thr Trp Asn Leu Leu Asp Phe Ser Thr Met Ile Ala
    210                 215                 220
Asp Asp Met Ser Asn Tyr Asp Glu Glu Gly Ala Trp Pro Val Leu Ile
225                 230                 235                 240
Asp Asp Phe Val Glu Phe Ala Arg Pro Gln Ile Ala Gly Thr Lys Ser
                245                 250                 255
Thr Thr Val

<210> SEQ ID NO 14
<211> LENGTH: 258
<212> TYPE: PRT
<213> ORGANISM: Homo sapiens

<400> SEQUENCE: 14

Ser Lys Gln Glu Phe Met Asp Gly Met Thr Glu Leu Gly Cys Asp Ser
1               5                   10                  15
Ile Glu Gln Leu Lys Ala Gln Ile Pro Lys Met Glu Gln Glu Leu Lys
            20                  25                  30
Glu Pro Gly Arg Phe Lys Asp Phe Tyr Gln Phe Thr Phe Asn Phe Ala
        35                  40                  45
Lys Asn Pro Gly Gln Lys Gly Leu Asp Leu Glu Asp Arg Lys Lys Leu
    50                  55                  60
Glu Gln Leu Tyr Asn Arg Tyr Lys Asp Pro Gln Asp Glu Asn Lys Ile
65                  70                  75                  80
Gly Ile Asp Gly Ile Gln Phe Cys Asp Asp Leu Ala Leu Asp Pro
                85                  90                  95
Ala Ser Ile Ser Val Leu Ile Ile Ala Trp Lys Phe Arg Ala Ala Thr
            100                 105                 110
Gln Cys Glu Phe Ser Lys Gln Glu Phe Met Asp Gly Met Thr Glu Leu
        115                 120                 125
Gly Cys Asp Ser Ile Glu Gln Leu Lys Ala Gln Ile Pro Lys Met Glu
    130                 135                 140
Gln Glu Leu Lys Glu Pro Gly Arg Phe Lys Asp Phe Tyr Gln Phe Thr
145                 150                 155                 160
Phe Asn Phe Ala Lys Asn Pro Gly Gln Lys Gly Leu Asp Leu Glu Met
                165                 170                 175
Ala Ile Ala Tyr Trp Asn Leu Val Leu Asn Gly Arg Phe Lys Phe Leu
            180                 185                 190
Asp Leu Trp Asn Lys Phe Leu Leu Glu His His Lys Arg Ser Ile Pro
```

```
              195                 200                 205
Lys Asp Thr Trp Asn Leu Leu Leu Asp Phe Ser Thr Met Ile Ala Asp
    210                 215                 220

Asp Met Ser Asn Tyr Asp Glu Glu Gly Ala Trp Pro Val Leu Ile Asp
225                 230                 235                 240

Asp Phe Val Glu Phe Ala Arg Pro Gln Ile Ala Gly Thr Lys Ser Thr
                245                 250                 255

Thr Val

<210> SEQ ID NO 15
<211> LENGTH: 19
<212> TYPE: DNA
<213> ORGANISM: artificial sequence
<220> FEATURE:
<223> OTHER INFORMATION: T7 polymerase promoter sequence (example 1)

<400> SEQUENCE: 15
taatacgact cactatagg                                                   19

<210> SEQ ID NO 16
<211> LENGTH: 19
<212> TYPE: DNA
<213> ORGANISM: artificial sequence
<220> FEATURE:
<223> OTHER INFORMATION: T3 polymerase promoter sequence

<400> SEQUENCE: 16
aattaaccct cactaaagg                                                   19

<210> SEQ ID NO 17
<211> LENGTH: 19
<212> TYPE: DNA
<213> ORGANISM: artificial sequence
<220> FEATURE:
<223> OTHER INFORMATION: oligonucleotide for PCR amplification (example
      3)

<400> SEQUENCE: 17
tcaatcagta tgtcgaccc                                                   19

<210> SEQ ID NO 18
<211> LENGTH: 19
<212> TYPE: DNA
<213> ORGANISM: artificial sequence
<220> FEATURE:
<223> OTHER INFORMATION: oligonucleotide for PCR amplification (example
      3)

<400> SEQUENCE: 18
ggaagaaatt ggggaaaca                                                   19

<210> SEQ ID NO 19
<211> LENGTH: 19
<212> TYPE: DNA
<213> ORGANISM: artificial sequence
<220> FEATURE:
<223> OTHER INFORMATION: oligonucleotide for PCR amplification (example
      3)

<400> SEQUENCE: 19
atcgagcgcc tcttcaatc                                                   19

<210> SEQ ID NO 20
<211> LENGTH: 19
```

```
<212> TYPE: DNA
<213> ORGANISM: artificial sequence
<220> FEATURE:
<223> OTHER INFORMATION: oligonucleotide for PCR amplification (example
      3)

<400> SEQUENCE: 20
tggtgtctcc atttgctga                                              19

<210> SEQ ID NO 21
<211> LENGTH: 19
<212> TYPE: DNA
<213> ORGANISM: artificial sequence
<220> FEATURE:
<223> OTHER INFORMATION: oligonucleotide for PCR amplification (example
      4)

<400> SEQUENCE: 21
atctgaagat ccgtccact                                              19

<210> SEQ ID NO 22
<211> LENGTH: 19
<212> TYPE: DNA
<213> ORGANISM: artificial sequence
<220> FEATURE:
<223> OTHER INFORMATION: oligonucleotide for PCR amplification (example
      4)

<400> SEQUENCE: 22
atgcacaatg ggtattttt                                              19

<210> SEQ ID NO 23
<211> LENGTH: 23
<212> TYPE: DNA
<213> ORGANISM: artificial sequence
<220> FEATURE:
<223> OTHER INFORMATION: oligonucleotide for PCR amplification (example
      5; forward primer to generate dsRNA 305A12)

<400> SEQUENCE: 23
ttcgtctcga acacgtatat cct                                         23

<210> SEQ ID NO 24
<211> LENGTH: 23
<212> TYPE: DNA
<213> ORGANISM: artificial sequence
<220> FEATURE:
<223> OTHER INFORMATION: oligonucleotide for PCR amplification (example
      5; reverse primer to generate dsRNA 305A12)

<400> SEQUENCE: 24
gaaagaagat gaatcaggca ttg                                         23

<210> SEQ ID NO 25
<211> LENGTH: 23
<212> TYPE: DNA
<213> ORGANISM: artificial sequence
<220> FEATURE:
<223> OTHER INFORMATION: oligonucleotide for PCR amplification (example
      5; forward primer to generate dsRNA 341G5)

<400> SEQUENCE: 25
ctgcaaaaat tatgactgtg tcg                                         23

<210> SEQ ID NO 26
<211> LENGTH: 21
<212> TYPE: DNA
```

```
-continued

<213> ORGANISM: artificial sequence
<220> FEATURE:
<223> OTHER INFORMATION: oligonucleotide for PCR amplification (example
      5; reverse primer to generate dsRNA 341G5)

<400> SEQUENCE: 26
agcattcaga tttggttgtc c                                              21
```